United States Patent
Arora et al.

(10) Patent No.: US 7,491,721 B2
(45) Date of Patent: Feb. 17, 2009

(54) ANTIMYCOBACTERIAL PHARMACEUTICAL COMPOSITION

(75) Inventors: Sudershan Kumar Arora, Pune (IN); Neelima Sinha, Pune (IN); Rakesh Sinha, Pune (IN); Ram Shankar Upadhyaya, Pune (IN)

(73) Assignee: Lupin Limited, Maharashtra (IN)

( * ) Notice: Subject to any disclaimer, the term of this patent is extended or adjusted under 35 U.S.C. 154(b) by 918 days.

(21) Appl. No.: 10/844,992

(22) Filed: May 12, 2004

(65) Prior Publication Data
US 2005/0256128 A1    Nov. 17, 2005

(51) Int. Cl.
*A61K 31/12* (2006.01)
*A61K 31/33* (2006.01)
*A61K 31/135* (2006.01)
*A61K 31/165* (2006.01)
*A61K 31/166* (2006.01)

(52) U.S. Cl. .......................... 514/252; 514/253; 514/355
(58) Field of Classification Search ............ 514/251.13, 514/253.09, 355
See application file for complete search history.

(56) References Cited

U.S. PATENT DOCUMENTS 5,227,383 A * 7/1993 Clark et al. .................. 514/288

* cited by examiner

*Primary Examiner*—Sreeni Padmanabhan
*Assistant Examiner*—Sahar Javanmard
(74) *Attorney, Agent, or Firm*—Ladas and Parry LLP

(57) ABSTRACT

An antimycobacterial combination and composition for treating tuberculosis are described. The compounds used are N-(3-[[4-(3-trifluoromethylphenyl)piperazinyl]methyl]-2-methyl-5-phenyl-pyrrolyl)-4-pyridylcarboxamide of formula (I) or a pharmaceutically acceptable non-toxic salt thereof

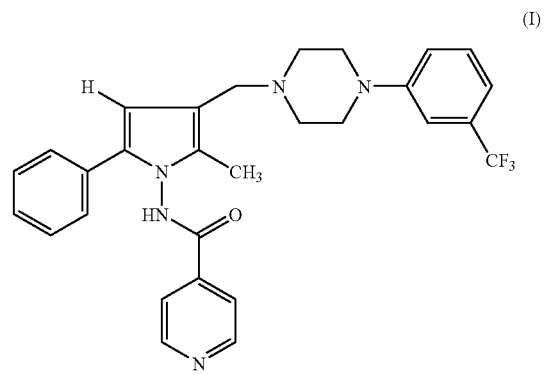

(I)

and an amount of one or more first line antitubercular drugs.

32 Claims, 3 Drawing Sheets
(3 of 3 Drawing Sheet(s) Filed in Color)

Fig-1 : Kill Curve Of Compound Of Formula (I) Against M. tuberculosis H₃₇Rv As determined By Viable Count Estimation method

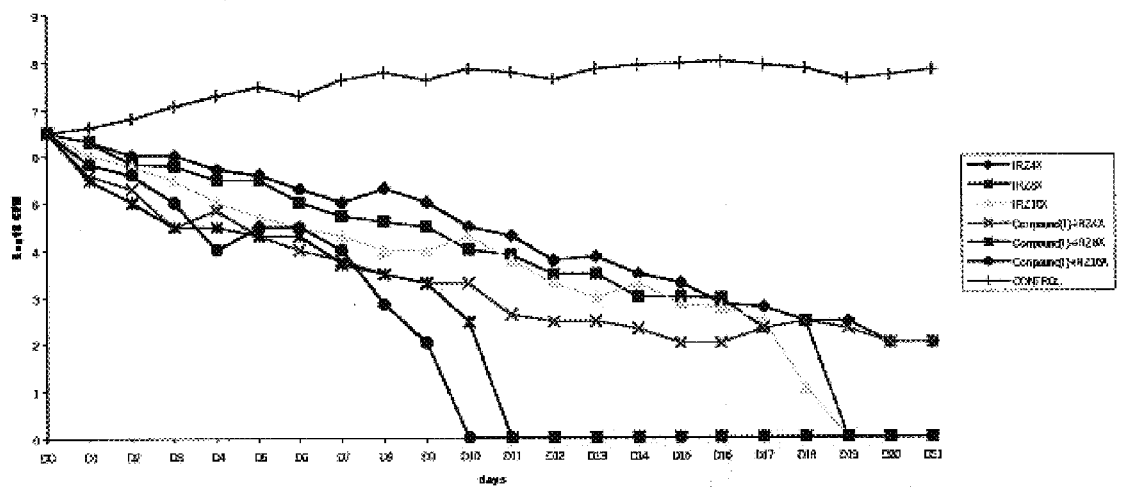
Fig-2: Kill Curve Of Compound Of Formula (I) In Combination With Known Antitubercular Drugs[Isonaizid (I); Rifampicin (R); and Pyrazinamide (Z)] Against *M. tuberculosis* As Determined by Viable Count Estimation Method

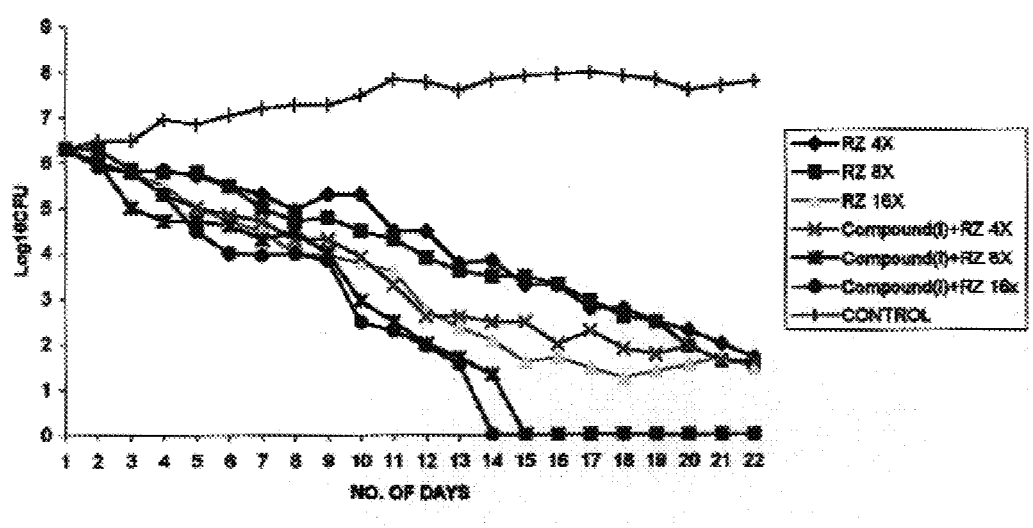
Fig-3 : Kill Curve of Compound Of Formula (I) In Combination With Known Antitubercular Drugs [Rifampicin (R) and Pyrazinamide (Z)] Without Isoniazid Against *M. tuberculosis* as Determined By Viable Count Estimation Method

ANTIMYCOBACTERIAL PHARMACEUTICAL COMPOSITION

FIELD OF THE INVENTION

The present invention relates to a combination comprising an effective amount of N-(3-[[4-(3-trifluoromethylphenyl)piperazinyl]methyl]-2-methyl-5-phenyl-pyrrolyl)-4-pyridylcarboxamide of formula (I) or a pharmaceutically acceptable salt thereof and one or more of first line antitubercular drugs for the treatment of tuberculosis, including multi-drug resistant varieties and latent tuberculosis.

The present invention also relates to a pharmaceutical composition, comprising a combination of an effective amount of N-(3-[[4-(3- trifluoromethylphenyl) piperazinyl]methyl]-2-methyl-5-phenyl-pyrrolyl)-4-pyridylcarboxamide of formula (I) or a pharmaceutically acceptable salt thereof with one or more of first line antitubercular drugs in admixture with one or more pharmaceutically acceptable excipients. The composition may be used for treatment of tuberculosis, including multi-drug resistant varieties and latent tuberculosis.

The present invention further relates to a method for treatment of tuberculosis, including multi-drug resistant varieties and latent tuberculosis.

BACKGROUND OF THE INVENTION

Worldwide, tuberculosis remains a leading cause of death. There are approximately 8 million active cases of tuberculosis per year, with 3 million deaths annually. About 1.7 billion people (one-third of world's population) are estimated to harbor the latent *Mycobacterium tuberculosis* infection [Kochi, A. *Tubercle.* 1991, 72, 1-6]. Individuals with latent tuberculosis carry 2 to 23% lifetime risk of reactivation of the disease later in life [Parrish, N M., Dick, J D., and Bishai, W R., *Trends. Microbial.* 1980, 6, 107-112]. In addition, immunosuppressive conditions including human immunodeficiency virus (HIV) infection has dramatically increased the risk of reactivation of tuberculosis.

The emergence of drug resistant pathogens renders the current mode of treatment very difficult and in many cases completely ineffective. Treatment of multi-drug resistant varieties of tuberculosis is difficult, and the disease often carries a high rate of mortality, particularly in developing countries. It is estimated that in the next twenty years over one billion people will be newly infected with tuberculosis with nearly 35 million people succumbing to the disease [WHO Fact Sheet No. 104, Global Alliance For TB Drug Development: Executive Summary of the Scientific Blueprint for TB Development; http://www.who.int/inf-fs/en/fact104.html]. With the emergence of HIV related tuberculosis, the disease is assuming alarming proportions as one of the killer diseases in the world today. The World Health Organization (WHO) has declared as a priority the need to immediately control tuberculosis infection for prevention of the spread of drug resistant strains.

One problem with current tuberculosis therapies is the shift of *M. tuberculosis* into a dormant or latent state. Thus, while the treatment of active tuberculosis with the currently prescribed combination drug regimen reduces the bacterial burden by a substantial amount, a proportion of *bacilli* shift into dormancy and survive in the host for months or years without producing any overt disease. However, later the *bacilli* can reactivate resulting in active tuberculosis once again. The recurrence of tuberculosis these days is considered to be the result of the reactivation of latent organisms which survive in the host [Stead, W W., *Am. Rev. Respir. Dis.,* 1982, 95, 729-745; Stead, W W., Kerby, G R., Schleuter, and Jordahl, C W., *Ann. Intern. Med.,* 1968, 68, 731-745].

The first drug used to combat *M. tuberculosis* was streptomycin in 1944, which was found to inhibit the growth of *M. tuberculosis*. A few classes of compounds have been introduced into clinical practice in the last 30 years, such as:

a) Long acting rifamycins e.g., rifapentine, rifabutin, and rifalazil [Javis, B., Lamb, H M., *Drugs,* 1998, 56, 607-616; McGregor, M M., Olliaro, P., Wolmarans, L., *Am. J. Respir. Crit. Care Med.,* 1996, 154, 1462-1467; Shoen, C M., DeStefano, M S., Cynamon, M H., *Clin. Infect. Dis.,* 2000, 30(Suppl. 3), S288-S29];

b) Fluoroquinolone compounds e.g. levofloxacin, moxifloxacin, and gatifloxacin [Ji, B., Lounis, N., Truffot-Pernot, C., Grosset., *Antimicrob. Agents Chemother.,* 1995, 39, 1341-1344; Miyazaki, E., Miyazaki, M., Chen, J M., Chaisson, R E., Bishai, W R., *Antimicrob. Agents Chemother.,* 1999, 43, 85-89; Fung-Tomc, J., Minassian, B., Kolek, B., Washo, T., Huczko, E., Boner, D., *Antimicrob. Agents Chemother.,* 2000, 45, 437-446];

c) Oxazolidinone compounds [Cynamon, M H., Klemens, S P., Sharpe, C A., Chase, S C., *Antimicrob. Agents Chemother.,* 1999, 43, 1189-1191]; and d) Niroimidazopyrans [Strover, C K., Warrener, P., VanDevabter, D., *Nature,* 2000, 405, 962-966].

However, none of these compounds has shown the desired potential to effectively treat multi-drug resistant and/or latent tuberculosis.

Rifapentine and rifalazil have shown effectiveness in treating tuberculosis through administration of lesser (intermittent therapy) doses of the drugs and a combination of the two drugs is also reported to be more effective in preventing latent tuberculosis than rifampicin. However, since these drugs have the same pharmacophore as rifampicin their activity spectrum against the resistant strains has not improved significantly. These molecules are rather ineffective against multi-drug resistant strains of *M. tuberculosis*. Further, many of these compounds have proved to be toxic.

A number of drugs, such as p-aminosaliscyclic acid, isoniazid, pyrazinamide, ethambutol, ethionamide, rifampicin etc. have been used either alone or in combination for treatment of tuberculosis. These drugs were found to be more effective than streptomycin in treating patients infected with the streptomycin resistant strains, thereby ushering in an era of effective treatment of tuberculosis.

Currently, the treatment of tuberculosis consists of administering a combination of four first line drugs, viz. isoniazid, rifampicin, ethambutol and pyrazinamide, administered individually as a single drug formulation or as a fixed dose combination. For effective treatment the abovementioned four first line drugs are given to a patient in the initial or induction phase, during which the drugs are used in combination to kill the rapidly multiplying population of *M. tuberculosis* as well as to prevent the emergence of drug resistance. This is followed by a continuation phase during which sterilizing drugs, viz. isoniazid, rifampicin, and pyrazinamide are given to kill the intermittently dividing population of *M. tuberculosis* [Jindani, A., Aber, V R., Edwards, E A., Mitchison, D A., *Am. Rev. Respir. Dis.,* 1980, 121, 39-49; Grosset, J., *Tubercule.,* 1978, 59, 287-297; East African/British Medical Research Council Study in *Am. Rev. Respir. Dis.,* 1977, 115, 3-8; Singapore Tuberculosis Service/British Medical Research Council in *Am. Rev. Respir. Dis.,* 1979, 119, 579-585; British Thoracic Society and Tuberculosis Association in *Am. Rev. Respir.*

*Dis.*, 1982, 126, 460-462; Snider, D E., Rogowski, J., Zierski, M., Bek, E., Long, M W., *Am. Rev. Respir. Dis.*, 1982, 125, 265-267].

While the abovemenioned combination of first line drugs together provide treatment against sensitive *M. tuberculosis* infection in 4 to 6 months time, such a combination therapy is not always successful, especially in patients harbouring multi-drug resistant strains. Also the long duration of treatment consisting of six months, more often than not, leads to unpleasant side effects. Further, compliance with the relatively long course of treatment is generally poor. Such non-compliance leads, more often than not, to treatment failure resulting in development of drug resistance.

The second line drugs, such as cycloserine, clofazimine, capreomycin etc. used for treatment, on the other hand, are more expensive, may cause severe side effects and are inferior to the first line drugs.

Substituted pyrrole derivatives constitute another class of compounds, which hold promise as antimycobacterial agents. Many pyrrole derivatives have been synthesized and tested for antitubercular activity [Deidda, D., et. al., *Antimicrob. Agents Chemother.*, 1998, 3035-3037; Biava, M., et. al., *J. Med. Chem Res.*, 1999, 19-34; Biava, M., et. al., *Bioorg. & Med. Chem. Lett.*, 1999, 2, 2983-2988; Cerreto, F., et. al., *Eur. J. Med. Chem.*, 1992, 27, 701-708; Gillet, C., et. al., *Eur. J. Med. Chem.-Chimica Therapeutica.*, 1976, 11(2), 173-181; Raagno. R., et. al., *Bioorg. & Med. Chem.*, 2000, 8, 1423-1432]. At best, the compounds disclosed therein are drug candidates not drugs since the reports contain no mention of in vivo activity and toxicity of the compounds disclosed therein against experimental tuberculosis in animal models. Hence, the compounds are more of academic rather than any commercial interest.

Hence, there is an urgent need to develop newer regimens that can be used to prevent, treat and/or reduce tuberculosis and/or eliminate the threat of multi-drug resistant tuberculosis and/or latent tuberculosis.

An alternative regimen should be superior to the existing regimen so as to:

a) shorten the total duration of treatment and/or significantly reduce the total number of doses;

b) provide an effective treatment of the multi-drug resistant varieties;

c) provide more effective treatment of latent tuberculosis; and d) minimize or prevent side effects.

In our PCT Application No. PCT/IN02/00189 (WO 04/026828 A1) we have described several substituted pyrrole derivatives and pharmaceutically acceptable salts thereof, which have demonstrated good to excellent inhibitory activity against the susceptible and drug resistant strains of *M. tuberculosis*. The MIC value of some of the most active compounds against sensitive and multi-drug resistant strains of *M. tuberculosis* were in the range of 0.12 to 0.5 µg/ml. Further, some of the compounds have also demonstrated therapeutically significant in vivo activity against *M. tuberculosis* infected animals and also found to be safe having an $LD_{50}$ value of about 700 mg/kg in mice as against 133 mg/kg for isoniazid. Moreover, the pharmacokinetic profile of the compounds are excellent. The subject matter of PCT Application No. PCT/IN02/00189 (WO 04/026828 A) is incorporated herein by reference.

The present inventors have found that a number of the pyrrole derivatives disclosed in PCT Application No. PCT/IN02/00189 (WO 04/026828 A1) provide a synergistic effect when used in combination with some of the front line drugs, thereby providing a new treatment of tuberculosis, including multi-drug resistant varieties and latent tuberculosis. The treatments described herein are superior to the drug regimens known in the prior art.

SUMMARY OF THE INVENTION

An aspect of the present invention is to provide a combination comprising one or more pyrrole derivatives disclosed in our PCT Application No. PCT/IN02/00189 (WO 04/026828 A1) and one or more of other antitubercular drugs for effective treatment of tuberculosis including multi-drug resistant varieties and latent tuberculosis.

A further object of the present invention is to provide a novel combination comprising a synergistically effective amount of a pyrrole derivative disclosed in PCT Application No. PCT/IN02/00189 (WO 04/026828 A1) and an effective amount of one or more first line antitubercular drugs.

Another aspect of the present invention is to provide a combination comprising one or more pyrrole derivatives disclosed in our PCT Application No. PCT/IN02/00189 (WO 04/026828 A1) and one or more of other antitubercular drugs, which is effective in the inhibition and/or treatment of mycobacterial conditions/cells including but not limited to one or more of sensitive and multi-drug resistant strains of *Mycobacterium tuberculosis, Mycobacterium avium*-intracellular complex, *M. fortutium, M. kansasaii* or other related mycobacterial species.

Still another aspect of the present invention is to provide an effective treatment of tuberculosis.

Yet another aspect is to reduce the treatment time from six months.

A still further aspect is provide a treatment of tuberculosis comprising administration to a patient in need thereof a combination comprising a pyrrole derivative disclosed in our PCT Application No. PCT/IN02/00189 (WO 04/026828 A1) and one or more of first line antitubercular drugs.

Yet another aspect is provide a treatment of tuberculosis that results in complete eradication of sensitive and drug resistant strains comprising administration to a patient in need thereof a combination comprising a pyrrole derivative disclosed in our PCT Application No. PCT/IN02/00189 (WO 04/026828 A1) and one or more of first line antitubercular drugs.

Still another aspect of the present invention is to provide an effective treatment of tuberculosis which results in complete eradication of sensitive and drug resistant *M. tuberculosis* comprising administration to a patient in need thereof a combination of a pyrrole derivative disclosed in our PCT Application No. PCT/IN02/00189 (WO 04/026828 A1) with one or more first line antitubercular drugs.

Yet another aspect of the present invention is to provide an effective treatment of tuberculosis which results in complete eradication of one or more sensitive and drug resistant strains such as *Mycobacterium tuberculosis, Mycobacterium avium*-intracellular complex, *M. fortutium, M. kansasaii* or other related mycobacterial species comprising administration to a patient in need thereof a combination comprising a pyrrole derivative disclosed in our PCT Application No. PCT/IN02/00189 (WO 04/026828 A1) and one or more of first line antitubercular drugs.

Another further aspect of the present invention is to provide a method for treatment and/or inhibition of one or more multi-drug resistant strains including but not limited to *M. tuberculosis Mycobacterium avium*-intracellular complex, *M. fortutium, M. kansasaii* and other related mycobacterial species comprising administration a pharmaceutical composition comprising a combination of a pyrrole derivative disclosed in PCT Application No. PCT/IN02/00189 (WO 04/026828 A1) with one or more first line antitubercular drugs to a patient in need thereof.

A further aspect of the present invention is to provide a method to prevent relapse of tuberculosis after the withdrawal of the treatment comprising administration to a patient in need thereof a combination comprising a pyrrole derivative disclosed in our PCT Application No. PCT/IN02/00189 (WO 04/026828 A1) and one or more of first line antitubercular drugs.

A further aspect of the present invention is to provide a method to prevent relapse of *M. tuberculosis* infection after the withdrawal of the treatment comprising administration to a patient in need thereof a combination comprising a pyrrole derivative disclosed in our PCT Application No. PCT/IN02/00189 (WO 04/026828 A1) and one or more of first line antitubercular drugs.

Another further aspect of the present invention is to provide a pharmaceutical composition comprising a combination of a pyrrole derivative disclosed in our PCT Application No. PCT/IN02/00189 (WO 04/026828 A1) with one or more of first line antitubercular drugs for effective treatment of tuberculosis including multi-drug resistant varieties and latent tuberculosis.

Yet another aspect of the present invention is to provide a pharmaceutical composition comprising a synergistically effective amount of the pyrrole derivatives disclosed in our PCT Application No. PCT/IN02/00189 (WO 04/026828 A1) in combination with an effective amount of one or more first line antitubercular drugs.

Yet another further aspect of the present invention is to provide a pharmaceutical composition comprising a combination of a pyrrole derivative disclosed in our PCT Application No. PCT/IN02/00189 (WO 04/026828 A1) with one or more first line antitubercular drugs, which is effective in inhibition and/or treatment of mycobacterial conditions/cells including but not limited to one or more sensitive and multi-drug resistant strains of *Mycobacterium tuberculosis, Mycobacterium avium*-intracellular complex, *M. fortutium, M. kansasaii* and other related mycobacterial species.

Another aspect of the present invention is to provide an effective treatment of tuberculosis comprising administration to a patient in need thereof a pharmaceutical composition comprising a combination of a pyrrole derivative disclosed in our PCT Application No. PCT/IN02/00189 (WO 04/026828 A1) with one or more first line antitubercular drugs.

Yet another aspect is provide a treatment of tuberculosis that results in complete eradication of sensitive and drug resistant strains comprising administration to a patient in need thereof a pharmaceutical composition comprising a pyrrole derivative disclosed in our PCT Application No. PCT/IN02/00189 (WO 04/026828 A1) and one or more of first line antitubercular drugs.

Still another aspect of the present invention is to provide an effective treatment of tuberculosis which results in complete eradication of sensitive and drug resistant *M. tuberculosis* comprising administration to a patient in need thereof a pharmaceutical composition comprising a combination of a pyrrole derivative disclosed in our PCT Application No. PCT/IN02/00189 (WO 04/026828 A1) with one or more first line antitubercular drugs.

Yet another aspect of the present invention is to provide an effective treatment of tuberculosis which results in complete eradication of one or more sensitive and drug resistant strains such as *Mycobacterium tuberculosis, Mycobacterium avium*-intracellular complex, *M. fortutium, M. kansasaii* or other related mycobacterial species comprising administration to a patient in need thereof a pharmaceutical composition comprising a combination comprising a pyrrole derivative disclosed in our PCT Application No. PCT/IN02/00189 (WO 04/026828 A1) and one or more of first line antitubercular drugs.

A further aspect of the present invention is to provide a method to prevent relapse of tuberculosis after the withdrawal of the treatment comprising administration to a patient in need thereof a pharmaceutical composition comprising a combination comprising a pyrrole derivative disclosed in our PCT Application No. PCT/IN02/00189 (WO 04/026828 A1) and one or more of first line antitubercular drugs.

A further object of the present invention is to provide a method to prevent relapse of *M. tuberculosis* infection after the withdrawal of the treatment comprising administration to a patient in need thereof a pharmaceutical composition comprising a combination of a pyrrole derivative disclosed in our PCT Application No. PCT/IN02/00189 (WO 04/026828 A1) with one or more first line antitubercular drugs.

Another further aspect of the present invention is to provide a method for treatment and/or inhibition of one or more multi-drug resistant strains including but not limited to *M. tuberculosis Mycobacterium avium*-intracellular complex, *M. fortutium, M. kansasaii* and other related mycobacterial species comprising administration a pharmaceutical composition comprising a combination of a pyrrole derivative disclosed in PCT Application No. PCT/IN02/00189 (WO 04/026828 A1) with one or more first line antitubercular drugs to a patient in need thereof.

Yet further object of the present invention is to provide a process for preparation of a composition comprising an effective amount of a pyrrole derivative disclosed in our PCT Application No. PCT/IN02/00189 (WO 04/026828 A1) in combination with an effective amount of one or more first line antitubercular drugs.

BRIEF DESCRIPTION OF THE FIGURES

The file of this patent contains at least one drawing or photograph executed in color. Copies of this patent with color drawing(s) or photograph(s) will be provided by the Patent and Trademark Office upon request and payment of necessary fee.

FIG. 1 shows a kill curve of a compound of formula (I) against *M. tuberculosis* $H_{37}Rv$.

FIG. 2 shows a kill curve of compound of formula (I) in combination with known antitubercular drugs.

FIG. 3 shows a kill curve of compound of formula (I) in combination with known antitubercular drugs.

DETAILED DESCRIPTION OF THE INVENTION

Unless defined otherwise, technical and scientific terms used herein have the same meaning as commonly understood by one of ordinary skill in the art in which this invention belongs. Any methods and materials similar or equivalent to those described herein can be used in the practice or testing of the present invention.

Unless stated to the contrary, any use of the words such as "including," "containing," "comprising," "having" and the like, means "including without limitation" and shall not be construed to limit any general statement that it follows to the specific or similar items or matters immediately following it.

Embodiments of the invention are not mutually exclusive, but may be implemented in various combinations. The described embodiments of the invention and the disclosed examples are given for the purpose of illustration rather than limitation of the invention as set forth the appended claims.

For purposes of the present invention, the following terms are defined below.

The terms "administering to", "administration of" and "administering a" compound, combination or composition should be understood to mean providing a compound, combination or composition or a prodrug of a compound to the patient in need of treatment.

The term "co-administration" as used herein is intended to encompass administration of the individual compounds present in the combination together or separately. Co-administration can also encompass combinations of administration of two or more of the compounds of the combination together with other of compounds of the combination being administrated separately or together or variations thereof. Separate administration of each compound, at different times and by different routes may also be considered co-administration. Co-adminstration can also include the combined administration of two or more compounds of the combination, if the route of administration of each individual compound is same. For example, if the route of administration of all the individual compounds is the same, eg. oral route then one or more of the individual compounds in the combination can be formulated into a dosage form suitable for the same route of administration. The term "co-administration" can also be construed to encompass to administration of one or more of the compounds of the combination together (e.g. in a single dosage form) or one or more of each compound separately.

The term "composition" as used herein is intended to encompass a product comprising the specified ingredients, as well as any product which results, directly or indirectly, from a combination of the specified ingredients. A "composition" may contain a single compound or more than one compound. A "composition" may contain one or more active ingredients.

The term "complete eradication" means there is no culturable *mycobacterium* after the designated incubation period in the target organs i.e. lungs or spleen of the infected animal or person following treatment according to this invention.

The term "excipient" means a component of a pharmaceutical product or composition that is not the active ingredient, such as a filler, diluent, carrier, and so on. The excipients that are useful in preparing a pharmaceutical composition are preferably pharmaceutically acceptable.

The term "pharmaceutically acceptable" as used herein means that the carrier, filler, diluent or excipient must be compatible with the other ingredients of the formulation and not deleterious to the recipient thereof.

The term "pharmaceutical composition" is intended to encompass a product comprising the active ingredient(s), pharmaceutically acceptable excipient(s) as well as any product which results, directly or indirectly, from combination, complexation or aggregation of any two or more of the ingredients, or from dissociation of one or more of the ingredients and/or excipients, or from other types of reactions or interactions of one or more of the ingredients and/or excipients. Accordingly, the pharmaceutical compositions of the present invention encompass any composition made by admixing the active ingredient, additional active ingredient(s), and pharmaceutically acceptable excipients.

The term "synergy" or "synergistic" includes but is not limited to (i) a quantity or amount, whereby a particular compound, active ingredient or drug can be administered in a lesser dosage when present in combination with one or more other active ingredients, compounds or drugs than the dosage required when it is administered individually; and/or (ii) nature/time, whereby a particular active ingredient, compound, or drug present in a combination either exhibits improved efficacy or results in reduced time of treatment than when it is administered individually.

Our PCT Application No. PCT/IN02/00189 (WO 04/026828 A1) discloses pyrrole derivatives, which exhibit antimycobacterial activity. These derivatives were found to be superior to those of previously known compounds as would be evident from their in vivo efficacy and low toxicity. Of all the ninety odd compounds disclosed therein, Compound No. 12, viz. N-(3-[[4-(3-trifluoromethylphenyl)piperazinyl]methyl]-2-methyl-5-phenyl-pyrrolyl)-4-pyridylcarboxamide and its pharmaceutically acceptable non-toxic salts, designated as compound of formula (I) in the present application, was found to exhibit excellent antimycobacterial activity against sensitive and multi-drug resistant strains of *M. tuberculosis*.

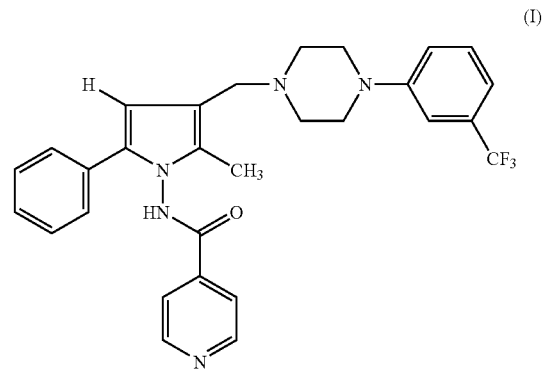

(I)

It should be noted that reference to a compound of formula (I) includes its non-toxic pharmaceutically acceptable acid addition salts thereof. Suitable salts are formed both with organic and inorganic acids and include those formed with maleic, fumaric, benzoic, ascorbic, pamoic, succinic, salicylic, methanesulfonic, ethanedisulfonic, acetic, propionic, tartaric, citric, gluconic, stearic, palmitic, itaconic, glycolic, p-aminobenzoic, glutamic, bensulfamic, benzenesulfonic, p-toluenesulfonic, phosphoric, sulfuric, nitric, hydrochloric, hydrobromic acids etc.

A therapeutically effective amount of the compound of formula (I) was found to possess the desired antitubercular properties. However, a synergistic effect is observed when a compound of formula (I) is co-administered with some of the first line antitubercular drugs, such as isoniazid, rifampicin, ethambutol and pyrazinamide. By synergistic effect it is meant the therapeutic effect of co-administering a compound of formula (I) and one or more of the first line antitubercular drugs, mentioned hereinabove above is greater than the therapeutic effect obtained on administration of an effective amount of either compound (I), or the therapeutic effective amount of any of the first line antitubercular drugs administered individually. Further, the therapeutic effect of co-administering a compound of formula (I) and one or more of the first line antitubercular drugs, mentioned hereinabove above is greater than the therapeutic effect obtained on administration of the first line antitubercular drugs, when administered in combination with one another.

Such synergy is advantageous in that it allows for administration of each of the components in the combination in an amount less than that would be required if administered individually. Thus the therapy can be affected for subjects who for example, do not respond adequately to the use of one component at the maximal strength dose.

Thus, co-administration of both the pyrrole compound of formula (I) and one or more of isoniazid, rifampicin, ethambutol and pyrazinamide was found to produce an effect, which results in improved treatment of tuberculosis as compared to the effect when the compound of formula (I) or the first line antitubercular drugs are administered individually or when the first line antitubercular drugs are administered in combination with one another.

Co-administration of both the pyrrole compound of formula (I) and one or more of isoniazid, rifampicin, ethambutol and pyrazinamide was found to produce an effect, which results in complete eradication of tuberculosis vis-à-vis incomplete eradication when the compound of formula (I) or the first line antitubercular drugs are administered individually or when the first line antitubercular drugs are administered in combination with one another.

The term, complete eradication" means no culturable mycobacterium could be observed in the target organs i.e. lungs or spleen of the infected animals after the treatment regimen with the combination of the present invention. It is noted that at the end of treatment of infected animals with the existing drug regimen i.e. a combination of one or more of the first line antitubercular drugs, viz. ethambutol, isoniazid, pyrazinamde and rifampicin a significantly culturable amount of tubercule *bacilli* is recovered from the target organs i. e, lungs and spleen. This would be evident from the data given in Tables-X, XI, and XII below.

One method for quantification of any culturable *mycobacterium* comprises sacrificing the treated animals at the end of the treatment regimen, wherein the target organs i.e. the lungs and spleen are aseptically removed, homogenized in sterile medium, and serial tenfold dilutions of the homogenate are then placed onto a media plate. The residual homogenate from the original tube is also plated on a media containing plate for enumeration of total count. No growth of mycobacteria after the incubation period is thus considered to mean complete eradication of *M. tuberculosis*. A person skilled in the art could use other known methods for quantification of culturable *mycobacterium*.

The current therapy for treating tuberculosis comprises providing a combination of isoniazid, rifampicin, pyrazinamide and ethambutol in amounts of 25.0, 20.0, 150.0 and 100.0 mg/kg of body weight respectively which amounts to an administration of a total of 295 mg/kg of the drugs[Enquire, J A F., Jann, L C., and Cynamon, M H., *Antimicrob Agents Chemother.* 2002, 46, 1022-1025; Anne, M J., Lenerts, A., Sharon, E C., Chemielewski A J., and Cynamon M H., *Antimicrob. Agents Chemother.*, 1999, 43, 2356-2360; Cynamon M H., and Klemens, S P., *Antimicrob. Agents Chemother.*, 1996, 40, 298-301]. In contrast, in one embodiment of this invention the therapy utilizing the compound of formula (I) in combination with the first line antitubercular drugs can be achieved with less than a total amount of 295 mg/kg of isonaizid, rifampicin, pyrazinamide and ethambutol. For example, in one embodiment a total amount of about 200 mg/kg of isofampicin, rifampicin, pyrazinamide and ethambutol may be administered, which is less than the amount used in the current therapy.

Additionally, by administering the individual components in lower amount, side effects can, in many cases, be minimized or avoided.

In short, the combination of co-administration of compound of formula (I) with one or more of the known first line antitubercular drugs adds a new dimension to the treatment of tuberculosis, hitherto not reported.

It was further found that the combination mentioned hereinbefore modulates the response to the drug resistant strains of *M. tuberculosis* and is "fast acting". Thus, the time taken to provide complete and effective eradication of *Mycobacterium* from a subject compared to that taken by the known drugs currently in practice, either taken alone or in combination with each other is reduced significantly. In one embodiment the treatment with the combination of this invention is found to take only one third the time taken for treatment comprising the currently prescribed regimen of a combination of the first line antitubercular drugs.

More significantly, our studies show that on administration of a combination of a compound of formula (I) with known antitubercular drugs like rifampicin and pyrazinamide there is an approximately twelve fold increase in the $C_{max}$ value of the compound of formula (I) in blood. Similar improvement is also observed for the T1/2 and AUC values.

Significantly, in one embodiment of the invention combinations of the compound of formula I or a pharmaceutically acceptable salt thereof and one or more of the first line antitubercular drugs was found to prevent the relapse of the mycobacterial infection after discontinuation of the treatment.

Separate administration of each compound, at different times and by different routes, in some cases would be advantageous. Thus, the components in the combination i.e. the pyrrole derivative of formula (I) and one or more of the first line antitubercular drugs need not be necessarily be administered at essentially same time or in any order. The administration can be so timed that the peak pharmacokinetic effect of one compound coincides with the peak pharmacokinetic effect of the other.

All the active ingredients can be formulated into separate or individual dosage forms which can be co-administered one after the other. Another option is that if the route of administration is the same (e.g. oral) two or more of the active compounds can be formulated into a single form for co-administration, both methods of co-administration, however, being part of the same therapeutic treatment or regimen.

In one embodiment of the invention, the pyrrole compound of formula (I) and the first line antitubercular drugs are co-administered orally and separately through suitable dosage forms.

The formulations, combinations and compositions of the present invention is effected using suitable pharmaceutically acceptable excipients.

The present invention provides an antimycobacterial combination comprising a therapeutically effective amount of N-(3-[[4-(3-trifluoromethylphenyl)piperazinyl]methyl]-2- methyl-5-phenyl-pyrrolyl)-4-pyridylcarboxamide of formula (I) or a pharmaceutically acceptable non-toxic salt thereof

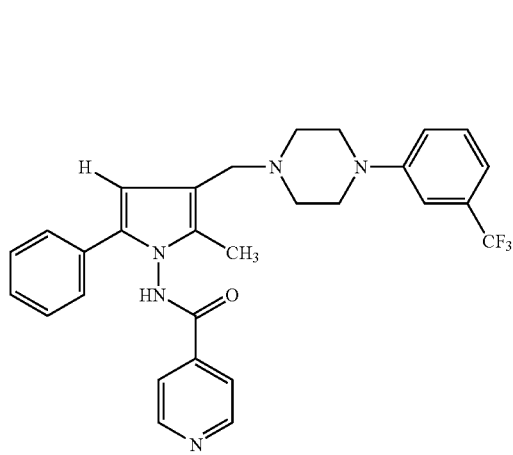

(I)

and a therapeutically effective amount of one or more first line antitubercular drugs selected from isoniazid, rifampicin, ethambutol and pyrazinamide for the treatment of tuberculosis.

In another aspect, the present invention provides an antimycobacterial combination comprising a therapeutically effective amount of N-(3-[[4-(3-trifluoromethylphenyl)piperazinyl]methyl]-2-methyl-5-phenyl-pyrrolyl)-4-pyridylcarboxamide of formula (I) or a pharmaceutically acceptable non-toxic salt thereof

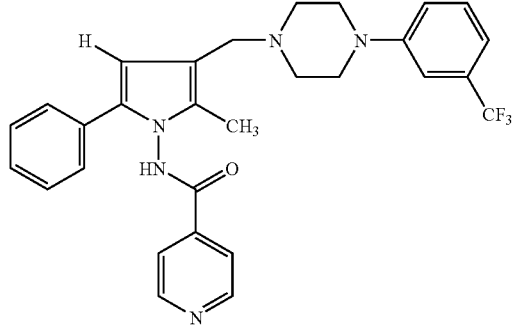

(I)

and a therapeutically effective amount of one or more first line antitubercular drugs selected from isoniazid, rifampicin, ethambutol and pyrazinamide for treatment of latent tuberculosis.

In yet another aspect, the present invention provides an antimycobacterial combination comprising a therapeutically effective amount of N-(3-[[4-(3-trifluoromethylphenyl)piperazinyl]methyl]-2-methyl-5-phenyl-pyrrolyl)-4-pyridylcarboxamide of formula (I) the compound of formula (I) or a pharmaceutically acceptable non-toxic salt thereof

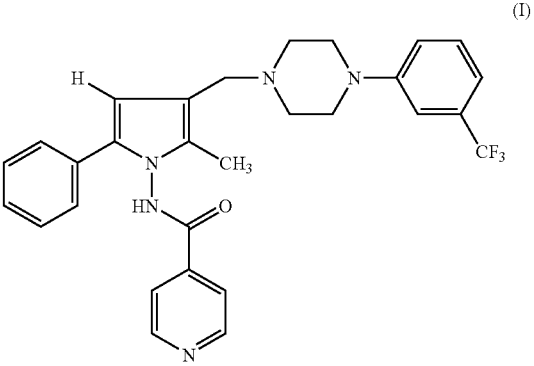

(I)

and a therapeutically effective amount of one or more first line antitubercular drugs selected from isoniazid, rifampicin, ethambutol and pyrazinamide for treatment of multi-drug resistant tuberculosis.

In a further aspect, the present invention provides an antimycobacterial combination comprising a therapeutically effective amount of N-(3-[[4-(3- trifluoromethylphenyl)piperazinyl]methyl]-2-methyl-5-phenyl-pyrrolyl)-4-pyridylcarboxamide of formula (I) or a pharmaceutically acceptable non-toxic salt thereof

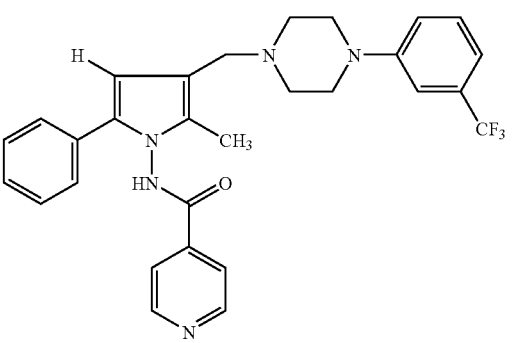

(I)

and a therapeutically effective amount of one or more first line antitubercular drugs selected from isoniazid, rifampicin, ethambutol and pyrazinamide for treatment and/or inhibition of one or more mycobacterial conditions/cells including but not limited to sensitive and multi-drug resistant strains of *Mycobacterium tuberculosis, Mycobacterium avium*-intracellular complex, *M. fortutium, M. kansasaii* and other related mycobacterial species.

The treatment of tuberculosis comprises co-administration to a patient in need theref the antimycobacterial combination comprising a therapeutically effective amount of N-(3-[[4-(3-trifluoromethylphenyl)piperazinyl]methyl]-2-methyl-5-phenyl-pyrrolyl)-4-pyridylcarboxamide of formula (I) or a pharmaceutically acceptable non-toxic salt thereof

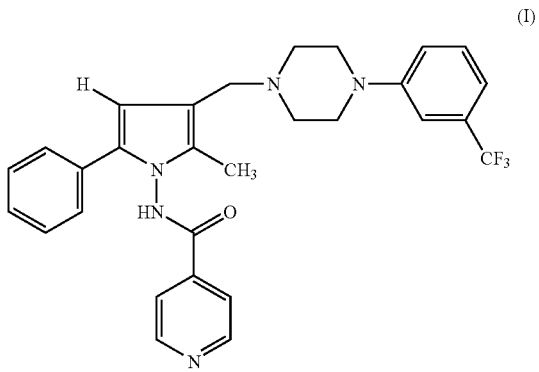

(I)

and a therapeutically effective amount of one or more first line antitubercular drugs selected form isoniazid, rifampicin, ethambutol.

In yet another further aspect, the present invention provides an effective treatment of tuberculosis in reduced treatment time.

In one example of the invention the treatment time is reduced to two to three months. In another example of the invention there is complete eradication of sensitive and drug resistant strains which cause tuberculosis. Examples of sensitive and drug resistant strains are *M. tuberculosis, Mycobacterium avium*-intracellular complex, *M. fortutium, M. kansasaii* and other related mycobacterial species.

In another further aspect, the present invention provides a method to prevent relapse of tuberculosis after the cessation of the treatment. The method comprises co-administration to a patient in need of an antimycobacterial combination comprising a therapeutically effective amount of N-(3-[[4-(3-trifluoromethylphenyl)piperazinyl]methyl]-2-methyl-5-phenyl-pyrrolyl)-4-pyridylcarboxamide of formula (I) or a pharmaceutically acceptable non-toxic salt thereof

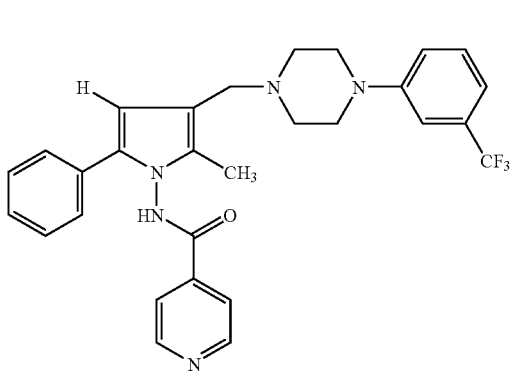

(I)

and a therapeutically effective amount of one or more of the first line antitubercular drugs selected from isoniazid, rifampicin, ethambutol and pyrazinamide.

The relapse may be the result of the reactivation of dormant or latent sensitive and multi-drug resistant strains of *Mycobacterium tuberculosis, Mycobacterium avium*-intracellular complex, *M. fortutium, M. kansasaii* and other related mycobacterial species.

In another aspect, the present invention provides a synergistic antimycobacterial combination comprising a synergistically effective amount of compound of N-(3-[[4-(3-trifluoromethylphenyl)piperazinyl]methyl]-2-methyl-5-phenyl-pyrrolyl)-4-pyridylcarboxamide of formula (I) or a pharmaceutically acceptable non-toxic salt thereof

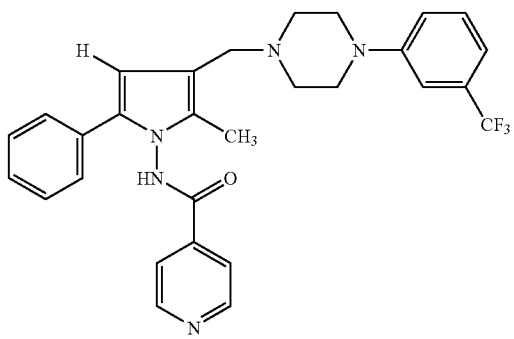

(I)

and a therapeutically effective amount of one or more first line antitubercular drugs selected from isoniazid, rifampicin, ethambutol and pyrazinamide for the treatment of tuberculosis including multi-drug resistant varieties and latent tuberculosis.

Another aspect of the invention is achieving a therapeutically synergistic effective treatment of tuberculosis comprising co-administering to a patient in need of such treatment an amount of:

(i) a compound of formula (I) or a pharmaceutically acceptable non-toxic salts thereof, and (ii) one or more of first line antitubercular drugs selected from isoniazid, rifampicin, ethambutol and pyrazinamide.

wherein the amount of (i) alone and the amount of isoniazid, rifampicin, ethambutol or pyrazinamide alone is insufficient to achieve the synergistic therapeutically effective level of treatment of tuberculosis but wherein the combined effect of the amount of (i) and one or more of isoniazid, rifampicin, ethambutol or pyrazinamide is greater than the sum of levels of the therapeutic effects of tuberculosis treatment achievable with the individual amounts of (i) and isoniazid, rifampicin, ethambutol or pyrazinamide.

In yet another aspect, the present invention provides an antimycobacterial pharmaceutical composition comprising a combination of a therapeutically effective amount of N-(3-[[4-(3-trifluoromethylphenyl)piperazinyl]methyl]-2-methyl-5-phenyl-pyrrolyl)-4-pyridylcarboxamide of formula (I) or a pharmaceutically acceptable non-toxic salt thereof

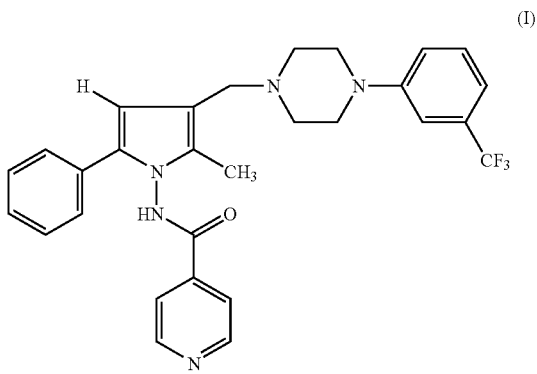

(I)

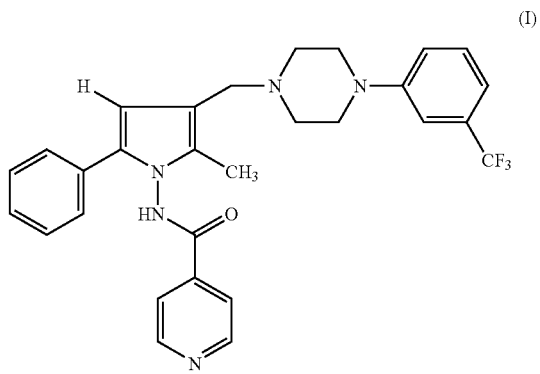

(I)

with a therapeutically effective amount of one or more first line antitubercular drugs selected form isoniazid, rifampicin, ethambutol and pyrazinamide and in admixture with a pharmaceutically acceptable excipient for the treatment of tuberculosis.

This composition can also be used for treatment of multi-drug resistant varieties and latent tuberculosis.

In a further aspect, the present invention provides an antimycobacterial pharmaceutical composition comprising a combination of a therapeutically effective amount of N-(3-[[4-(3-trifluoromethylphenyl)piperazinyl]methyl]-2-methyl-5-phenyl-pyrrolyl)-4-pyridylcarboxamide of formula (I) or a pharmaceutically acceptable non-toxic salt thereof

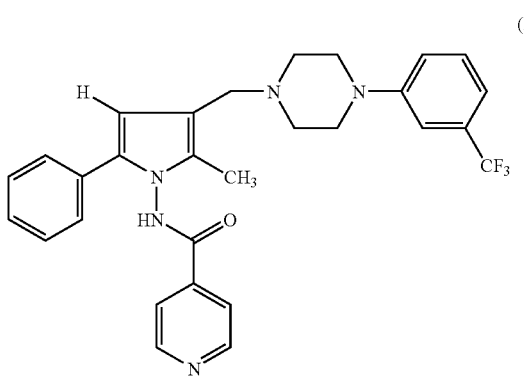

(I)

with a therapeutically effective amount of one or more first line antitubercular drugs selected form isoniazid, rifampicin, ethambutol and pyrazinamide and in admixture with a pharmaceutically acceptable excipient for treatment and/or inhibition of one or more mycobacterial conditions/cells including but not limited to sensitive and multi-drug resistant strains of *Mycobacterium tuberculosis, Mycobacterium avium*-intracellular complex, *M. fortutium, M. kansasaii* and other related mycobacterial species.

In another further aspect, the present invention provides a method that is useful in preventing relapse of tuberculosis infection after the cessation of the treatment comprising co-administration to a patient in need thereof an antimycobacterial pharmaceutical composition comprising a combination of a therapeutically effective amount of N-(3-[[4-(3-trifluoromethylphenyl)piperazinyl]methyl]-2-methyl-5-phenyl-pyrrolyl)-4-pyridylcarboxamide of formula (I) or a pharmaceutically acceptable non-toxic salt thereof with a therapeutically effective amount of one or more first line antitubercular drugs selected from isoniazid, rifampicin, ethambutol and pyrazinamide and in admixture with a pharmaceutically acceptable excipient.

The relapse may be the result of the reactivation of dormant or latent sensitive and multi-drug resistant strains of *Mycobacterium tuberculosis, Mycobacterium avium*-intracellular complex, *M. fortutium, M. kansasaii* and other related mycobacterial species In yet another further aspect, the present invention provides a effective treatment of tuberculosis which not only reduces the treatment time to two to three months but results in complete eradication of sensitive and drug resistant *M. tuberculosis* comprising co-administration to a patient in need thereof of an antimycobacterial pharmaceutical composition comprising a combination of a therapeutically effective amount of N-(3-[[4-(3-trifluoromethylphenyl)piperazinyl]methyl]-2-methyl-5-phenyl-pyrrolyl)-4-pyridylcarboxamide of formula (I) or a pharmaceutically acceptable non-toxic salt thereof

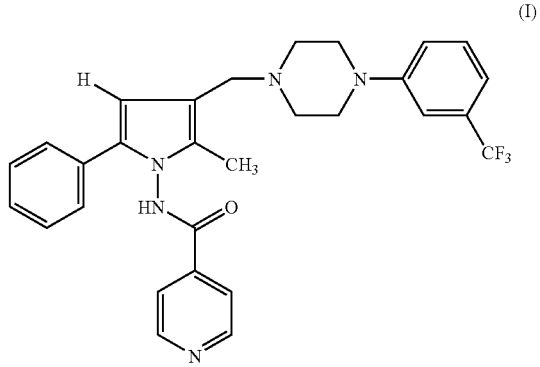

(I)

with a therapeutically effective amount of one or more first line antitubercular drugs selected form isoniazid, rifampicin, ethambutol and pyrazinamide and in admixture with one or more pharmaceutically acceptable excipients.

In another aspect, the present invention provides a synergistic antimycobacterial pharmaceutical composition comprising a combination of a synergistically effective amount of N-(3-[[4-(3-trifluoromethylphenyl)piperazinyl]methyl]-2-methyl-5-phenyl-pyrrolyl)-4-pyridylcarboxamide of formula (I) or a pharmaceutically acceptable non-toxic salt thereof

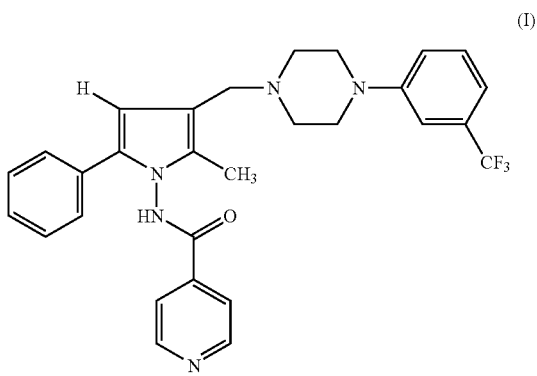

(I)

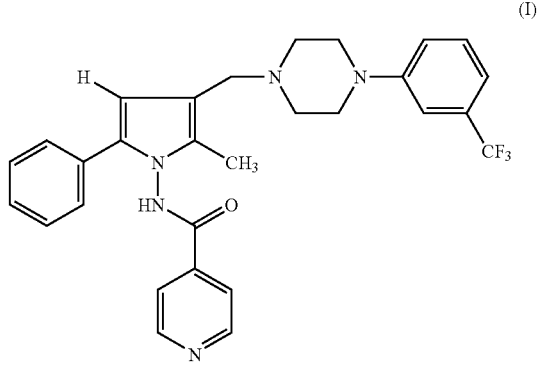

(I)

with a therapeutically effective amount of one or more first line antitubercular drugs selected form isoniazid, rifampicin, ethambutol and pyrazinamide and in admixture with one or more pharmaceutically acceptable excipients for the treatment of tuberculosis including multi-drug resistant varieties and latent tuberculosis.

In yet another aspect, the present invention provides a method for treatment and/or inhibition of one or more multi-drug resistant strains selected from but not limited to *M. tuberculosis Mycobacterium avium*-intracellular complex, *M. fortutium, M. kansasaii* and other related mycobacterial species comprising administering a combination of a therapeutically effective amount of N-(3-[[4-(3-trifluoromethylphenyl)piperazinyl]methyl]-2-methyl-5-phenyl-pyrrolyl)-4-pyridylcarboxamide of formula (I) or a pharmaceutically acceptable non-toxic salt thereof

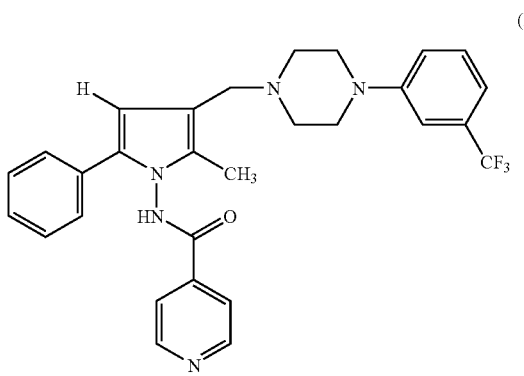

(I)

with a therapeutically effective amount of one or more first line antitubercular drugs selected form isoniazid, rifampicin, ethambutol and pyrazinamide and in admixture with a pharmaceutically acceptable excipient.

In a further aspect, of the present invention provides a process for preparation of an antimycobacterial pharmaceutical composition comprising a combination of a therapeutically effective amount of N-(3-[[4-(3-trifluoromethylphenyl) piperazinyl]methyl]-2-methyl-5-phenyl-pyrrolyl)-4-pyridylcarboxamide of formula (I) or a pharmaceutically acceptable non-toxic salt thereof with a therapeutically effective amount of one or more first line antitubercular drugs selected form isoniazid, rifampicin, ethambutol and pyrazinamide in admixture with one or more pharmaceutically acceptable excipients for treatment of tuberculosis including multi-drug resistant varieties and latent tuberculosis. A pharmaceutical composition comprising a combination of N-(3-[[4-(3-trifluoromethylphenyl)piperazinyl]methyl]-2-methyl-5-phenyl-pyrrolyl)-4-pyridylcarboxamide of formula (I) or a pharmaceutically acceptable non-toxic salt thereof with one or more first line antitubercular drugs may be preferably administered orally. Oral administration may be achieved through a tablet form comprising the above ingredients in admixture with one or more pharmaceutically acceptable excipients. Oral formulations are useful in providing accurate dosage, rapid dispensing and importantly encouraging patient compliance.

The pharmaceutically acceptable excipients that can be employed in the formulations or compositions include one or more of antioxidants, fillers, inert diluents, surfactants and conventional additives such as lubricating agents and opacifiers.

The antioxidants which can be used include but are not limited to ascorbic acid, butylated hydroxyanisole, butylated hydroxytoluene, fumaric acid, malic acid, propylgallate, sodium ascorbate, sodium metabisulfite etc.

The inert diluents which can be used include but are not limited to calcium carbonate, calcium sulfate, dextrates, dibasic calcium phosphate, hydrogenated vegetable oil, magnesium carbonate, magnesium oxide, mannitol, microcrystalline cellulose, polymethacrylates, powdered cellulose, pregelatinized starch, sorbitol, starch, tribasic calcium phosphate etc.

The surfactants which can be used include but are not limited to ionic surfactants like docusate sodium (dioctyl sodium sulfosuccinate), sodium lauryl sulfate etc. or nonionic surfactants like glyceryl monooleate, polyoxyethylene etc. or sorbitan fatty acid esters like polysorbate 80, polyvinyl alcohol etc.

Suitable lubricants which can be used in the pharmaceutical composition include but are not limited to magnesium stearate, sodium stearyl fumarate, hydrogenated vegetable oil, hydrogenated castor oil, hydrogenated cottonseed oil, stearic acid and calcium stearate, colloidal silicon dioxide and the like.

The lubricant is selected such that it provides an effective lubricating effect. For example, a typical formulation can contain from 0% to 10% percent by weight of the lubricant. In an embodiment the formulation contains from 0.2% to 2% percent by weight of the lubricant.

Suitable opacifiers which can be used in the pharmaceutical composition include but are not limited to titanium dioxide, talc, colloidal silicon dioxide etc.

The pharmaceutical composition in a fixed dose combination comprising a compound of formula (I) and one or more of the antitubercular compounds and pharmaceutically acceptable carriers can be prepared by conventional methods in the art. For e.g., a tablet form of the combination can be prepared by any one of the following non-limiting techniques, viz.

i) Dry Granulation Method: This method comprises sifting of the respective active ingredients and the pharmaceutical excipients, followed by granulation of the resulting powder mixture by compression in the absence of heat and solvent [Pharmaceutical Dosage Forms: Tablets, Vol. I, Page 173, ed. H. A. Lieberman, Marcel Dekker Inc., 1980].

ii) Wet Granulation Method: This method comprises sifting of the respective active ingredients and the pharmaceutical excipients and the resulting particles are stuck together using an adhesive to produce a granular product with improved flow properties and an increased ability to cohese under pressure.

iii) Direct Compression Method: This method comprises direct compression of the respective active ingredients and the pharmaceutical excipients without any preliminary treatment [The Pharmaceutical Codex, Principle and Practice of Pharmaceutics; page 10, ed. W. Lund, The Council of the Royal Pharmaceutical Society of Great Britain].

Some examples of the present invention, are combinations and the pharmaceutical compositions which encompass the following non-limiting mixtures, viz.

a) A compound of formula (I) or a pharmaceutically acceptable non-toxic salt thereof and rifampicin.

b) A compound of formula (I) or a pharmaceutically acceptable non-toxic salt thereof and isoniazid.

c) A compound of formula (I) or a pharmaceutically acceptable non-toxic salt thereof, isoniazid and rifampicin.

d) A compound of formula (I) or a pharmaceutically acceptable non-toxic salt thereof, isoniazid, rifampicin and pyrazinamide.

e) A compound of formula (I) or a pharmaceutically acceptable non-toxic salt thereof, pyrazinamide and ethambutol.

f) A compound of formula (I) or a pharmaceutically acceptable non-toxic salt thereof, rifampicin and pyrazinamide.

Other examples of the present invention, are combinations and the pharmaceutical compositions that encompass the following non-limiting mixtures, viz.

g) 12.5 or 25.0 mg/kg of a compound of formula (I) or a pharmaceutically acceptable non-toxic salt thereof and 20.0 mg/kg of rifampicin.

h) 12.5 or 25.0 mg/kg of a compound of formula (I) or a pharmaceutically acceptable non-toxic salt thereof and 25.0 mg/kg of isoniazid.

i) 12.5 or 25.0 mg/kg of a compound of formula (I) or a pharmaceutically acceptable non-toxic salt thereof and 25.0 mg/kg of isoniazid and 20.0 mg/kg of rifampicin.

j) 12.5 or 25.0 mg/kg of a compound of formula (I) or a pharmaceutically acceptable non-toxic salt thereof, 25.0 mg/kg of isoniazid, 20.0 mg/kg of rifampicin and 150.0 mg/kg of pyrazinamide.

k) 12.5 or 25.0 mg/kg of a compound of formula (I) or a pharmaceutically acceptable non-toxic salt thereof, 150.0 mg/kg of pyrazinamide and 100.0 mg/kg of ethambutol.

l) 3.12, 6.25 or 12.5 mg/kg of a compound of formula (I) or a pharmaceutically acceptable non-toxic salt thereof, 250.0 mg/kg of isoniazid, 20.0 mg/kg of rifampicin and 150.0 mg/kg of pyrazinamide.

m) 3.12, 6.25 or 12.5 mg/kg of a compound of formula (I) or a pharmaceutically acceptable non-toxic salt thereof, 20.0 mg/kg of rifampicin and 150.0 mg/kg of pyrazinamide.

Synthesis of Compound of Formula (I)

The compound of formula (I) and the pharmaceutically acceptable salts thereof can be synthesized by any known method including but not limited to the methods disclosed in our PCT Application No. PCT/IN02/00189 (WO 04/026828 A1), which is incorporated herein by reference.

An example of the preparation of N-(3-[[4-(3-trifluoromethylphenyl) piperazinyl]methyl]-2-methyl-5-phenyl-pyrrolyl)-4-pyridylcarboxamide is as follows:

Preparation of N-(3-[[4-(3-trifluoromethylphenyl) piperazinyl]methyl)]-2-methyl-5-phenylpyrrolyl)-4-pyridylcarboxamide Step 1

1-(4-chlorophenyl)pentane-1,4-dione

To a well stirred suspension of anhydrous aluminium chloride (27.0 gm, 205.9 mmol) in 126 ml. of chlorobenzene was added oxopentanoylchloride (23.0 gm, 171.6 mmol) dropwise, over a period of 30-35 minutes at room temperature (25-30° C.). The reaction mixture was stirred at the same temperature for 1 hour. After decomposition of the reaction mixture by the addition of solid ice and hydrochloric acid (10 ml) the precipitated solid was filtered and the filtrate evaporated on a rotary evaporator to remove all the solvents. The residue was dissolved in ethyl acetate (400 ml.), washed with water (2×100 ml.), brine (100 ml.) and dried over anhydrous sodium sulfate and the solvent evaporated off. The crude product so obtained was chromatographed over silica gel (100-200 mesh) using chloroform as eluent to give 8.6 gm (24.07%) of the title compound.

Step 2

N-(5-methyl-2-phenylpyrrolyl)-4 pyridylcarboxamide

A mixture of 1-(chlorophenyl)pentane-1,4-dione (6.0 g, 28.50 mmol, as obtained in Step-1) and isonicotinic hydrazide (4.30 gm, 31.35 mmol) in benzene (6.0 ml.) was refluxed by over molecular sieves. After two hours, benzene was removed under reduced pressure and the residue dissolved in ethyl acetate, washed with water (2×100 ml.) and brine (1×50 ml.). The ethyl acetate layer was dried over anhydrous sodium sulfate and the solvent evaporated off. The crude product so obtained as purified by column chromatography over silica gel (100-200 mesh) using 0.2% methanol in chloroform as eluent to give 3.50 gm (39.42%) of the title compound.

Step 3

N-(3-{[4-(3-trifuoromethylphenyl)piperazinyl]methyl}-2-methyl-5-phenylpyrrolyl)-4-pyridylcarboxamide To a stirred solution of N-(5-methyl-2-phenylpyrrolyl)-4-pyridylcarboxamide (0.300 gm, 1.083 mmol, as obtained in Step-2) in acetonitrile (5.0 ml.) was added a mixture of 1-(3-trifluoromethylphenyl)piperazine hydrochloride (0.288 gm, 1.083 mmol), 40% formaldehyde (0.032 gm, 1.083 mmol) and acetic acid (0.09 ml), drop-wise. After the completion of addition, the reaction mixture was stirred at room temperature for 4 hours. The reaction mixture was neutralized with sodium hydroxide (20% aq. Soln.) and extracted with ethyl acetate (2×50 ml.).

The combined ethyl acetate extract was washed with water (2×25 ml.), brine (1×20 ml.), and dried over anhydrous sodium sulfate and the solvent evaporated off. TLC of the crude product indicated two spots, which were separated by column chromatography over silica gel (100-200 mesh).

The more polar compound a eluted out using 80% ethyl acetate-hexane mixture was obtained in 24.34% (0.130 gm) and was identified as N-(3-{[4-(3-trifluoromethylphenyl)piperazinyl]methyl}-2-methyl-5-phenylpyrrolyl)-4-pyridylcarboxamide m.p. 80-82° C., MS: m/z 520 (M+1)

$^1$H NMR(CDCl$_3$, δ): 2:13 (s, 3H, CH$_3$), 2.60 (bs, 4H, 2×N—CH$_2$), 3.18 (bs, 4H, 2×N—CH$_2$), 3.41 (s, 2H, N—CH$_2$), 6.24 (s, 1H, H-4), 6.97-7.03 (4H, m, ArH), 7.22-7.29 (m, 5H, ArH), 7.53 (d, 2H, J=6 Hz, pyridyl ring), 8.50 (bs, 1H, NH D$_2$O exchangeable), 8.70 (d, 2H, J=6 Hz, pyridyl ring).

Pharmacological Testing

The preliminary antimycobacterial activity of the compound of formula (I) has been reported in our co-pending PCT Application No. PCT/IN02/00189. Further microbiological, toxicological and pharmacokinetic studies were carried out and are detailed hereinbelow. The compound of formula I that was used in the tests described below is the hydrochloride salt of the compound of formula (I) (hydrochloride salt of N-(3-[[4-(3-trifluoromethylphenyl)piperazinyl]methyl]-2-methyl-5-phenyl-pyrrolyl)-4-pyridylcarboxamide)).

In Vitro Studies

Agar Dilution Assay to Determine Minimal Inhibitory Concentrations

MIC of the individual compounds against strains of *mycobacterium* was determined by a reference agar dilution method as per the NCCLS-M24-T2 recommendations. The compounds were dissolved in DMSO and diluted two fold to obtain ten serial dilutions of each compound. An appropriate volume of the compounds was incorporated into duplicate plates of Middle brook 7H10 agar medium supplemented with 10% Middle brook supplement oleic acid-albumin-dextrose (OADC) enrichment at a concentration of 0.03 µg/ml to 16 µg/ml. Test organisms (*mycobacterium* strains) were grown in Middle brook 7H9 broth containing 0.05% Tween-80 and 10% ADC supplement. After 7 days of incubation at 37° C. the broths were adjusted to the turbidity of 1.0 McFarland standard; the organism were further diluted 10 fold in sterile water containing 0.10% Tween-80. The resulting mycobacterial suspensions were spotted (3-5 µl/spot) onto drug supplemented 7H10 media plates. The plates were sealed and incubated at 37° C. for 3-4 weeks in an upright position. The MIC was recorded as the lowest dilution of the compound that completely inhibited the growth of test organisms. Test isolates included clinical isolates that were generally sensitive/resistant to one or more standard anti tubercular drugs. Appropriate reference strains and control drug were included in each batch of the test.

Antimycobacterial Activity of Compound of Formula (I)

The in vitro activity exhibited by the hydrochloride salt of the compound of formula (I) (hydrochloride salt of N-(3-[[4-(3-trifluoromethylphenyl)piperazinyl]methyl]-2-methyl-5-phenyl-pyrrolyl)-4-pyridylcarboxamide) against approximately 200 sensitive and resistant clinical isolates of *M. tuberculosis* is summarized in Table-I.

TABLE I

In vitro Antimycobacterial Activity Of Compound of Formula (I) Against Clinical Isolates of *M. tuberculosis*

| Sr. No. | Compound/Drug | MIC (µg/ml) against *M. tuberculosis* isolates | | |
|---|---|---|---|---|
| | | Range | MIC50 | MIC90 |
| 1 | Compound of formula (I) | 0.12-0.5 | 0.12 | 0.25 |
| 2 | Isoniazid | 0.12->16.0 | 4 | >16.0 |
| 3 | Rifampicin | 0.12->16.0 | 4 | >16.0 |

Mycobactericidal Activity of Compound of Formula (I)

To determine whether the inhibitory activity of the compound of formula (I) is cidal or static the *M. tuberculosis* culture was incubated in the presence of different concentrations (1×, 2×, 4×, 8×, 16 MIC) of the compound of formula (I). A fixed volume (0.1 ml) of the culture was withdrawn from all the flasks daily for 21 days. The sample was then diluted ten fold and spotted on to Middle brook 7H10 medium for enumeration of tubercle *bacilli*.

A concentration and time showing 3 log reduction in *M. tuberculosis* count compared to untreated control was considered as cidal concentration. The compound of formula (I) was found to exhibit dose dependent killing of *M. tuberculosis* and hence determined to be cidal (3 log reduction in viable counts) at 8× and 16×MIC concentration. The kill curve of compound of formula (I) against of *M. tuberculosis* H37 Rv strain determined by the variable count estimation method is depicted in FIG. 1.

Synergistic Studies

The synergistic effect of the compound of formula (I) in the combination was determined using a micro broth checkerboard assay in combination with known antitubercular drugs. To test for synergy, serial dilution of the compound of formula (I) was added to a mycobacterial culture in the presence of another antitubercular drug viz. isoniazid, rifampicin, ethambutol and moxifloxacin. After 28 days all plates were read for complete absence of growth in the walls containing different drug combinations. The highest dilution of the combination not showing visible growth was considered as the MIC value of that combination. A compound was considered to possess synergy with another drug if the MIC of the individual compound improves by four fold or more.

The compound of formula (I) was found to exhibit synergistic activity in the in vitro broth micro dilution assay with rifampicin, additive effect with ethambutol but was not found to be affected in presence of isoniazid as summarized in Table-II.

TABLE II

In vitro Synergy Of Compound of Formula (I)
With Known Antitubercular Drugs By Micro Broth Dilution Method

| COMPOUND | | INTERPRETATION |
|---|---|---|
| Compound of formula (I) | ISONIAZID | INDIFFERENT |
| Compound of formula (I) | RIFAMPICIN | SYNERGY |
| Compound of formula (I) | ETHAMBUTOL | ADDITIVE |
| Compound of formula (I) | MOXIFLOXACIN | ANTAGONISTIC |

In Vivo Studies Alone or in Combination

The efficacy of the compound of formula (I) was also evaluated in murine model of pulmonary tuberculosis. *Mycobacterium tuberculosis* cultures were grown in Middle Brook 7H9 broth containing 0.05% Tween-80 and 10% ADC supplement at 37° C. for 7 days. For animal inoculation liquid culture was declumped by brief sonication and settling and were diluted appropriately in 7H9 broth to obtain a concentration of $1 \times 10^7$ CFU's/0.2 ml.

Four-week-old female out bred Swiss albino mice housed in a pathogen free, biosafety level 3 environments within micro isolator cages were used throughout the study. Infections were produced by intravenous inoculation into the caudal tail vein of 0.2 ml of declumped *M. tuberculosis* suspension. Following infection mice were randomly distributed in different groups of six each. Treatment began 14 days after infection. For treatment the compound of formula (I) and isoniazid were dissolved in sterile water and rifampicin was dissolved in 10% DMSO and diluted in water. The drugs were prepared every morning prior to administration. Therapy was given 5/7 days per week for one month. All the agents were administered by gavages and were dosed at 50, 25, or 12.5 mg/kg of body weight. The control group of infected but untreated mice was killed at the initiation of therapy (early control) or at the end of the treatment period (late control). Mice were sacrificed by cervical dislocation 5 days after the administration of the last dose of drug. The spleens and right lung were removed aseptically and homogenized in tissue homogeniser. At least 4-6 serial ten fold dilutions of the homogenate were plated onto selective Middle brook 7H11 agar plates induplicate. The colony counts were recorded after incubation at 37° C. for 4 weeks. The viable cell counts were converted to $Log_{10}$ values. A compound showing 2 Log reduction in viable counts compared to the controls was considered significant.

Long term in vivo experiments were conducted to evaluate the activity of compound of formula (I) in mono therapy and in combination with first line antitubercular drugs like Isoniazid, rifampicin, ethambutol, and pyrazinamide. In these studies the efficacy of different combination was evaluated at different time points i.e., one, two, three months of treatment.

Results of In Vivo Efficacy Studies

It was observed that monotherapy with the compound of formula (I) resulted in significant (>2log) reduction in viable *bacilli* in the target organs as compared to control animals as given in Table-III.

The compound of formula (I) demonstrated a 2 log reduction in the organs of the animals that were treated with 12.5 mg./kg body weight dose in animals infected with sensitive/resistant strains of *M. tuberculosis*, whereas isoniazid gave similar reduction in bacterial load at concentrations 25 mg/kg or more against sensitive strain but was not effective against resistant strains up to 50 mg/kg.

Further, studies to determine the long-term effect of treatment (two to three months) with compound of formula (I) were found to result in a decrease of the mycobacterial load in the target organs. Complete absence of *mycobactrium* was seen in 33% of the animals treated for three months. The results are summarized in Table-IV and Table-V respectively.

TABLE III

In vivo Efficacy Of Compound of Formula (I) After One Month Of Treatment In Mice
Model Infected With The Sensitive And Resistant Strains Of *M. tuberculosis*.

| Sr. No. | Compound | Mean $Log_{10}$CFU in organs of mice infected with sensitive strain of MTB | | Mean $Log_{10}$CFU in organs of mice infected with resistant strain of MTB | |
|---|---|---|---|---|---|
| | | Lung | Spleen | Lung | Spleen |
| 1 | Compound of formula (I) | | | | |
| | 12.5 mg/kg | 2.5 ± 0.35 | 2.89 ± 0.32 | 2.97 ± 0.53 | 3.02 ± 0.22 |
| | 25 mg/kg | 2.3 ± 0.63 | 2.42 ± 0.15 | 2.70 ± 0.36 | 2.54 ± 0.20 |
| | 50 mg/kg | 2.1 ± 0.36 | 2.28 ± 0.38 | 2.59 ± 0.22 | 2.32 ± 0.39 |
| 2 | Isoniazid | | | | |
| | 12.5 mg/kg | 4.56 ± 0.24 | 4.93 ± 0.42 | 5.47 ± 0.54 | 5.01 ± 0.45 |
| | 25 mg/kg | 3.19 ± 0.6 | 3.08 ± 0.44 | 5.34 ± 0.34 | 4.97 ± 0.52 |
| | 50 mg/kg | 2.97 ± 0.46 | 2.89 ± 0.27 | 4.77 ± 0.61 | 4.83 ± 0.68 |
| 3 | Control (Untreated) | 5.59 ± 0.29 | 5.95 ± 0.42 | 5.33 ± 0.37 | 5.25 ± 0.41 |

TABLE IV

In vivo Efficacy Of Compound Of Formula (I) In Mice Model Treated For Two Months

| | Compound | Mean $Log_{10}$CFU in organs of mice infected with sensitive strain of MTB | | Mean $Log_{10}$CFU in organs of mice infected with resistant strain of MTB | |
|---|---|---|---|---|---|
| | | Lung | Spleen | Lung | Spleen |
| 8 Weeks Treatment | Compound of formula (I) | | | | |
| | 50 mg/kg | 2.20 ± 0.56 | 2.17 ± 0.46 | 2.51 ± 0.72 | 2.37 ± 0.61 |
| | 25 mg/kg | 2.89 ± 0.73 | 2.37 ± 0.68 | 2.83 ± 0.66 | 2.61 ± 0.56 |
| | 12.5 mg/kg | 3.44 ± 0.69 | 2.75 ± 0.63 | 3.32 ± 0.6 | 3.1 ± 1.13 |
| | Isoniazid | | | | |
| | 50 mg/kg | 2.45 ± 0.60 | 2.30 ± 0.38 | 5.42 ± 0.74 | 5.1 ± 0.61 |
| | 25 mg/kg | 3.01 ± 0.68 | 2.68 ± 0.89 | 5.91 ± 0.35 | 5.7 ± 0.34 |
| | 12.5 mg/kg | 3.9 ± 0.45 | 3.73 ± 0.52 | 6.01 ± 0.9 | 5.88 ± 0.41 |
| | Control | | | | |
| | Early | 5.81 ± 0.32 | 5.6 ± 0.75 | 5.67 ± 0.35 | 5.74 ± 0.39 |
| | Late | 6.95 ± 0.36 | 6.69 ± 0.46 | 7.03 ± 0.18 | 6.95 ± 0.29 |

TABLE V

In vivo Efficacy of Compound Of Formula (I) In Mice Model Treated For Three Months

| | Compound | Mean $Log_{10}$CFU in organs of mice infected with sensitive strain of MTB | | Mean $Log_{10}$CFU in organs of mice infected with resistant strain of MTB | |
|---|---|---|---|---|---|
| | | Lung | Spleen | Lung | Spleen |
| 12 Weeks Treatment | Compound of formula (I) | | | | |
| | 50 mg/kg | 1.46 ± 1.06 | 1.56 ± 1.12 | 1.79 ± 0.92 | 1.69 ± 0.88 |
| | 25 mg/kg | 1.71 ± 1.24 | 1.63 ± 0.98 | 1.86 ± 0.97 | 1.79 ± 0.92 |
| | 12.5 mg/kg | 2.76 ± 0.53 | 2.68 ± 0.27 | 2.51 ± 0.18 | 2.6 ± 0.34 |
| | Isoniazid | | | | |
| | 50 mg/kg | 2.07 ± 0.33 | 2.68 ± 0.36 | 4.76 ± 0.20 | 5.64 ± 066 |
| | 25 mg/kg | 3.06 ± 0.83 | 2.41 ± 0.69 | 4.79 ± 0.55 | 5.62 ± 0.63 |
| | 12.5 mg/kg | 3.94 ± 0.28 | 3.9 ± 0.37 | 5.1 ± 0.7 | 5.72 ± 0.17 |
| | Control | | | | |
| | Early | 5.8 ± 0.32 | 5.6 ± 0.25 | 5.67 ± 0.35 | 5.74 ± 0.38 |
| | Late | 7.1 ± 0.41 | 7.16 ± 0.23 | 7.2 ± 0.23 | 7.46 ± 0.27 |

Pharmacokinetic Studies

Preliminary Pharmacokinetics studies of the compound of formula (I) was performed in mice and dog to determine bioavailibility and serum levels achieved and maintained by the compounds.

The results of the study summarized in Table-VI demonstrate that compound of formula (I) is bioavailable (56.40%) and has better half life and $C_{max}$ than isoniazid and is retained in the serum for longer time at concentration >MIC value.

TABLE VI

Pharmacokinetic Data Of Compound Of Formula (I) In Mice And Dogs

| Compound | Animal | Dose/route | $T_{max}$ (Hr) | $T_{1/2}$ (Hr) | $C_{max}$ | $AUC_{last}$ | Absolute bioavailability |
|---|---|---|---|---|---|---|---|
| Formula (I) | Mice | 25.0 mg | 2.00 | 3.41 | 2.68 | 6.88 | — |
| | Mice | (Oral) | 1.50 | 5.34 | 0.66 | 2.21 | — |
| | Dog | 12.5 mg | 3.48 | — | 8.65 | 19.98 | — |
| | Dog | (Oral) 12.5 mg (I.V.) 12.5 mg (Oral) | 0.75 | 5.07 | 3.384 | 10.64 | 56.40 |

Toxicity Studies

Acute toxicity of the compound of formula (I) was determined in rodents by oral route. The $LD_{50}$ was found to be 700 mg/kg in mice and 793 mg/kg in rats which is better than the $LD_{50}$ of isoniazid. The results are summarized in Table-VII.

TABLE VII

Preliminary Acute Toxicity (Oral Route) Studies On Compound Of Formula (I)

| Sr. No. | Compound | Animal | $LD_{50}$ values (mg/kg) |
|---|---|---|---|
| 1 | Formula (I) | Mice | 700 |
| 2 | Formula (I) | Rats | 793 |

In addition, compound of formula (I) was found to be non mutagenic for all the bacterial strains used in the Ames Mutagenicity test.

Experiments to Demonstrate the Antimycobacterial Activity of Compound of Formula (I) in Combination with One or More Antitubercular Drugs In Vitro Activity of the Combination The cidal effect of the combination of the compound of formula (I) of the with one or more first line antitubercular drug was determined in terms of dose and time taken for treatment.

The combination of compound of formula (I) with isoniazid, rifampicin and pyrazinamide (LIRZ) was found to exert mycobactericidal (FIG. 2) effect at 8 and 16×MIC on day 10 whereas combination of isoniazid, rifampicin and pyrazinamide without compound of formula (I) [IRZ] produced cidal effect only on day 20.

A kill curve of the compound of formula (I) in combination with known antitubercular drugs[Isonaizid (I); Rifampicin (R); and Pyrazinamide (Z)] against M. tuberculosis as determined by Viable Count Estimation Method is depicted in FIG. 2.

Further, similar effect on the mycobactericidal activity was observed in the combination of compound of formula (I) with rifampicin and pyrazinamide without isoniazid comprising compound 'A' The combination demonstrated mycobactericidal activity at 8 and 16×MIC on day 14.

A kill curve of compound of formula (I) in combination with known antitubercular drugs[Rifampicin (R) and Pyrazinamide (Z)], without isoniazid against M. tuberculosis as determined by Viable Count Estimation Method is depicted in FIG. 3.

In Vivo Activity of the Combination

In the mice treated with a combination of compound of formula (I) and one or more of first line antitubercular drugs a significant reduction in the load of tubercle bacilli was observed in all the combinations tested. Maximum reduction was observed in the animals treated with a combination of compound of formula (I) with two or three antitubercular drugs eg. compound (I) in combination with isoniazid and rifampicin and in combination with isoniazid, rifampicin and pyrazinamide after one month.

The observed in vivo efficacy of the combination of compound of formula (I) with known antitubercular drugs in mice model after treatment for one month is summarized in Table-VIII.

Further, treatment for two months resulted in absence of growth in the organs of 66% of the animals infected with sensitive/resistant strains of M. tuberculosis treated with combination of compound of formula (I) with two or three known antitubercular compounds like isoniazid, rifampicin and pyrazinamide.

The observed in vivo efficacy of the combination of compound of formula (I) with known antitubercular drugs in mice model after treatment for two months is summarized in Table-IX.

Further, treatment for three months showed complete absence of growth on the animals infected with sensitive/resistant strains of M. tuberculosis treated with combination of compound of formula (I) with two or three known antitubercular compounds like isoniazid, rifampicin and pyrazinamide.

The observed in vivo efficacy of the combination of compound of formula (I) with known antitubercular drugs in mice model after treatment for three months is summarized in Table-X.

Significantly, lower doses of compound of formula (I) i.e. 12.5, 6.25, and 3.12 mg/kg in combination with the known antitubercular drugs, viz. isoniazid, rifampicin and pyrazinamide is found to exhibit excellent in vivo efficacy and completely sterilize the organs of animals infected with sensitive/resistant strains of M. tuberculosis after two months of treatment. The results are summarized in Table-XI.

TABLE VIII

In vivo Efficacy Of Compound Of Formula (I) In Combination With Known Anti tubercular Drugs In Mice Model Treated For One Month

| Combination | Dose (mg/kg) | Mean $Log_{10}$CFU in organs of mice infected with sensitive strain of MTB | | Mean $Log_{10}$CFU in organs of mice infected with resistant strain of MTB | |
|---|---|---|---|---|---|
| | | Lung | Spleen | Lung | Spleen |
| (I) + INH | 12.5 + 25.0 | 3.10 ± 0.48 | 2.62 ± 0.34 | 2.81 ± 0.46 | 2.72 ± 0.28 |
| (I) + INH | 25.0 + 25.0 | 3.05 ± 0.44 | 2.33 ± 0.20 | 2.57 ± 064 | 2.52 ± 0.59 |
| (I) + RIF | 12.5 + 20.0 | 3.24 ± 0.54 | 2.73 ± 0.34 | 2.39 ± 0.55 | 2.47 ± 0.55 |
| (I) + RIF | 25 + 20.0 | 3.08 ± 0.4 | 2.52 ± 0.60 | 2.34 ± 0.34 | 2.18 ± 0.43 |
| (I) + INH + RIF | 12.5 + 25.0 + 20.0 | 3.02 ± 0.43 | 2.95 ± 0.39 | 1.97 ± 0.37 | 2.38 ± 099 |
| (I) + INH + RIF | 25.0 + 25.0 + 20.0 | 3.39 ± 0.32 | 2.94 ± 042 | 2.21 ± 0.58 | 2.35 ± 0.90 |
| (I) + INH + RIF + PYR | 12.5 + 25.0 + 20.0 + 150.0 | 2.83 ± 0.46 | 2.22 ± 0.33 | 2.99 ± 0.32 | 2.49 ± 0.39 |
| (I) + INH + RIF + PYR | 25.0 + 25.0 + 20.0 + 150.0 | 2.84 ± 0.48 | 2.10 ± 0.36 | 2.73 ± 0.43 | 2.33 ± 0.24 |
| (I) + ETH + PYR | 12.5 + 100.0 + 150.0 | 3.55 ± 0.32 | 2.85 ± 0.33 | 3.27 ± 0.42 | 2.80 ± 0.24 |
| (I) + ETH + PYR | 25.0 + 100.0 + 150.0 | 3.28 ± 0.52 | 2.30 ± 0.40 | 3.22 ± 018 | 2.57 ± 0.38 |
| INH | 25.0 | 3.20 ± 0.45 | 2.78 ± 0.30 | 5.23 ± 0.27 | 4.61 ± 0.43 |
| RIF | 20.0 | 2.75 ± 0.36 | 2.78 ± 0.42 | 3.05 ± 0.43 | 2.44 ± 0.32 |
| INH + RIF | 25.0 + 20.0 | 3.09 ± 0.33 | 3.04 ± 0.36 | 3.31 ± 0.32 | 2.82 ± 0.29 |
| INH + RIF + PYR | 25.0 + 20.0 + 150.0 | 3.17 ± 0.33 | 2.95 ± 0.29 | 3.18 ± 0.27 | 3.05 ± 0.37 |
| ETH + PYR | 100.0 + 150.0 | 3.51 ± 0.13 | 3.25 ± 0.33 | 3.47 ± 0.30 | 3.05 ± 0.36 |
| (I) | 25.0 | 3.11 ± 0.38 | 2.42 ± 0.4 | 2.86 ± 0.37 | 2.25 ± 0.18 |
| EARLY CONTROL | | 5.62 ± 0.72 | 5.23 ± 0.38 | 5.41 ± 0.63 | 5.13 ± 0.68 |
| LATE CONTROL | | 7.02 ± 0.25 | 6.51 ± 0.56 | 6.93 ± 0.42 | 6.76 ± 0.58 |

(I) = Compound of Formula (I);
INH = Isoniazid;
RIF = Rifampicin;
PYR = Pyrazinamide;
ETH = Ethambutol

TABLE IX

In vivo Efficacy Of Compound of Formula (I) In Combination With Known Anti tubercular Drugs In Mice Model Treated For Two Months

| Combination | Dose (mg/kg) | Mean $Log_{10}$CFU in organs of mice infected with sensitive strain of MTB | | Mean $Log_{10}$CFU in organs of mice infected with resistant strain of MTB | |
|---|---|---|---|---|---|
| | | Lung | Spleen | Lung | Spleen |
| (I) + INH | 12.5 + 25.0 | 1.58 ± 1.1 | 1.71 ± 0.91 | 2.23 ± 0.66 | 1.99 ± 0.95 |
| (I) + INH | 25.0 + 25.0 | 1.19 ± 0.9 | 1.32 ± 1.06 | 2.29 ± 0.2 | 1.78 ± 0.92 |
| (I) + RIF | 12.5 + 20.0 | 1.39 ± 1.12 | 1.18 ± 0.96 | 2.42 ± 1.2 | 1.53 ± 1.17 |
| (I) + RIF | 25.0 + 20.0 | 0.99 ± 1.01 | 1.76 ± 0.99 | 1.97 ± 1.23 | 1.32 ± 0.94 |
| (I) + INH + RIF | 12.5 + 25.0 + 20.0 | 0.96 ± 1.0 | 1.51 ± 1.1 | 1.52 ± 1.03 | 1.34 ± 1.15 |
| (I) + INH + RIF | 25.0 + 25.0 + 20.0 | 0.74 ± 1.16 | 1.06 ± 0.82 | 1.82 ± 0.95 | 1.81 ± 1.11 |
| (I) + INH + RIF + PYR | 12.5 + 25.0 + 20.0 + 150.0 | 0.92 ± 0.76 | 0.70 ± 0.50 | 1.20 ± 1.15 | 1.35 ± 1.09 |
| (I) + INH + RIF + PYR | 25.0 + 25.0 + 20.0 + 150.0 | 0.71 ± 0.62 | 1.10 ± 0.94 | 0.98 ± 1.01 | 1.31 ± 1.03 |
| (I) + ETH + PYR | 12.5 + 100.0 + 150.0 | 2.34 ± 0.78 | 2.22 ± 1.2 | 3.42 ± 0.78 | 3.89 ± 0.63 |
| (I) + ETH + PYR | 25.0 + 100.0 + 150 | 2.48 ± 0.78 | 2.61 ± 0.52 | 3.16 ± 0.68 | 3.37 ± 0.58 |
| INH | 25.0 | 1.91 ± 0.9 | 2.43 ± 0.39 | 5.15 ± 0.42 | 5.36 ± 0.84 |
| RIF | 20.0 | 1.84 ± 0.95 | 2.40 ± 0.7 | 2.45 ± 1.15 | 2.60 ± 0.59 |
| INH + RIF | 25.0 + 20.0 | 1.63 ± 1.03 | 2.28 ± 0.63 | 2.91 ± 1.05 | 3.13 ± 0.5 |
| INH + RIF + PYR | 25.0 + 20.0 + 150.0 | 1.41 ± 0.95 | 3.13 ± 0.98 | 1.89 ± 1.16 | 2.18 ± 1.08 |
| ETH + PYR | 100.0 + 150.0 | 3.23 ± 0.57 | 4.06 ± 0.74 | 4.13 ± 0.44 | 4.18 ± 0.48 |
| (I) | 25.0 | 1.86 ± 0.94 | 2.60 ± 0.45 | 2.37 ± 0.81 | 2.52 ± 0.48 |
| EARLY CONTROL | | 6.01 ± 0.48 | 6.47 ± 0.36 | 6.1 ± 0.34 | 6.38 ± 0.47 |
| LATE CONTROL | | 7.20 ± 0.54 | 6.96 ± 0.72 | 7.5 ± 0.35 | 7.21 ± 0.49 |

(I) = Compound of Formula (I);
INH = Isoniazid;
RIF = Rifampicin;
PYR = Pyrazinamide;
ETH = Ethambutol

TABLE X in vivo Efficacy Of Compound Of Formula (I) In Combination With Known Anti tubercular Drugs In Mice Model Treated For Three Months

| Combination | Dose (mg/kg) | Mean $Log_{10}$CFU in organs of mice infected with sensitive strain of MTB | | Mean $Log_{10}$CFU in organs of mice infected with resistant strain of MTB | |
|---|---|---|---|---|---|
| | | Lung | Spleen | Lung | Spleen |
| (I) + INH | 12.5 + 25.0 | 1.42 ± 1.16 | 1.39 ± 1.1 | 2.24 ± 0.44 | 1.90 ± 1.07 |
| (I) + INH | 25.0 + 25.0 | 0.62 ± 0.95 | 0.95 ± 1.04 | 2.34 ± 1.18 | 1.19 ± 0.93 |
| (I) + RIF | 12.5 + 20.0 | 0.61 ± 0.95 | 0.64 ± 0.99 | 0.99 ± 1.09 | 0.82 ± 0.92 |
| (I) + RIF | 25.0 + 20.0 | 0.47 ± 0.62 | 0.63 ± 0.97 | 0.95 ± 1.05 | 0.62 ± 0.95 |
| (I) + INH + RIF | 12.5 + 25.0 + 20.0 | 0.32 ± 0.55 | 0.55 ± 0.68 | 0.28 ± 0.67 | 0.25 ± 0.60 |
| (I) + INH + RIF | 25.0 + 25.0 + 20.0 | 0.00 | 0.00 | 0.00 | 0.26 ± 0.63 |
| (I) + INH + RIF + PYR | 12.5 + 25.0 + 20.0 + 150.0 | 0.00 | 0.00 | 0.00 | 0.00 |
| (I) + INH + RIF + PYR | 25.0 + 25.0 + 20.0 + 150.0 | 0.00 | 0.00 | 0.00 | 0.00 |
| (I) + ETH + PYR | 12.5 + 100.0 + 150.0 | 1.51 ± 1.16 | 1.64 ± 1.10 | 2.36 ± 1.02 | 1.79 ± 1.40 |
| (I) + ETH + PYR | 25.0 + 100.0 + 150.0 | 1.28 ± 1.00 | 1.14 ± 0.92 | 1.75 ± 0.73 | 1.39 ± 1.05 |
| INH | 25.0 | 1.20 ± 0.98 | 1.35 ± 1.09 | 5.37 ± 0.35 | 5.19 ± 0.65 |
| RIF | 20.0 | 0.84 ± 1.10 | 1.21 ± 0.83 | 0.94 ± 1.04 | 1.78 ± 1.38 |
| INH + RIF | 25.0 + 20.0 | 0.78 ± 0.88 | 0.94 ± 1.05 | 0.58 ± 0.9 | 1.16 ± 1.30 |
| INH + RIF + PYR | 25.0 + 20.0 + 150.0 | 0.67 ± 1.05 | 0.59 ± 0.92 | 0.62 ± 0.96 | 0.75 ± 1.17 |
| ETH + PYR | 100.0 + 150.0 | 1.85 ± 1.04 | 2.82 ± 0.28 | 2.12 ± 1.06 | 2.21 ± 1.16 |
| (I) | 25.0 | 0.82 ± 0.91 | 1.09 ± 0.83 | 1.30 ± 1.02 | 1.64 ± 1.12 |
| EARLY CONTROL | | 6.22 ± 0.46 | 5.87 ± 0.52 | 6.28 ± 0.25 | 6.20 ± 0.53 |
| LATE CONTROL | | 7.32 ± 0.39 | 7.37 ± 0.48 | 7.31 ± 0.38 | 7.20 ± 0.44 |

(I) = Compound of Formula (I);
INH = Isoniazid;
RIF = Rifampicin;
PYR = Pyrazinamide;
ETH = Ethambutol

TABLE XI

In vivo Efficacy Of Compound Of Formula (I) In Combination With Known Anti tubercular Drugs (Isoniazid, Rifampicin and Pyrazinamide) In Mice Model Against *M. tuberculosis* (sensitive and resistant strains) After Two Months Treatment

| Sr. No. | Compound (mg/kg) | Mean $Log_{10}$CFU in organs of mice infected with sensitive strain of MTB | | Mean $Log_{10}$CFU in organs of mice infected with resistant strain of MTB | |
|---|---|---|---|---|---|
| | | Lung | Spleen | Lung | Spleen |
| 1 | (I) in Combination with INH + RIF + PYR | | | | |
| | 12.5 | 0.00 | 0.00 | 0.00 | 0.00 |
| | 6.25 | 0.23 + 0.72 | 0.2 + 0.63 | 0.441 + 0.94 | 0.49 + 1.035 |
| | 3.12 | 2.468 + 0.495 | 2.72 + 0.28 | 2.84 + 0.66 | 2.92 + 0.43 |
| 2 | INH + RIF + PYR | 2.99 + 0.37 | 3.20 + 0.22 | 4.34 + 0.59 | 3.802.45 |
| 3 | Control | | | | |
| | Early | 6.037 ± 0.45 | 5.66 ± 0.68 | 5.76 ± 027 | 5.53 ± 0.40 |
| | Late | 7.30 + 0.35 | 7.04 + 0.21 | 7.037 + 0.39 | 6.95 + 0.39 |

(I) = Compound of Formula (I);
INH = Isoniazid;
RIF = Rifampicin;
PYR = Pyrazinamide Further, the effect in in vivo efficacy on continued treatment of infected animals with the combination of the compound of formula (I) with isoniazid, rifampicin and pyrazinamide are summarized in Table-XII.

The effect in in vivo efficacy on treatment of mice with another combination comprising the compound of formula (I) with two known antitubercular compounds, viz. rifampicin and pyrazinamide for two months was also found be effective in reducing the mycobacterial load from the target organs as shown in Table-XIII.

TABLE XII

In vivo Efficacy Of Compound Of Formula (I) In Combination With Known Anti tubercular Drugs (Isoniazid, Rifampicin and Pyrazinamide) In Mice Model Against *M. tuberculosis* (sensitive and resistant strains) After Three Months Treatment

| Sr. No. | Compound (mg/kg) | Mean $Log_{10}$CFU in organs of mice infected with sensitive strain of MTB | | Mean $Log_{10}$CFU in organs of mice infected with resistant strain of MTB | |
|---|---|---|---|---|---|
| | | Lung | Spleen | Lung | Spleen |
| 1 | (I) in Combination with INH + RIF + PYR | | | | |
| | 12.5 | 0.00 | 0.00 | 0.00 | 0.00 |
| | 6.25 | 0.00 | 0.00 | 0.00 | 0.00 |
| | 3.12 | 1.562 + 1.05 | 1.387 + 0.97 | 2.34 + 0.78 | 2.22 + 1.2 |
| 2 | INH + RIF + PYR | 1.55 + 1.00 | 1.33 + 0.93 | 3.87 + 0.59 | 3.17 + 0.45 |
| 3 | Control | | | | |
| | Early | 6.037 ± 0.45 | 5.66 ± 0.68 | 5.76 ± 027 | 5.53 ± 0.40 |
| | Late | 7.83 + 0.35 | 7.46 + 0.33 | 7.74 + 0.54 | 7.28 + 0.68 |

(I) = Compound of Formula (I);
INH = Isoniazid;
RIF = Rifampicin;
PYR = Pyrazinamide;

TABLE XIII

In vivo Efficacy Of Compound of Formula (I) In Combination With Known Anti tubercular Drugs (Rifampicin and Pyrazinamide) In Mice Model Against *M. tuberculosis* (sensitive and resistant strains) After Two Months Treatment

| Sr. No. | Compound (mg/kg) | Mean $Log_{10}$CFU in organs of mice infected with sensitive strain of MTB | | Mean $Log_{10}$CFU in organs of mice infected with resistant strain of MTB | |
|---|---|---|---|---|---|
| | | Lung | Spleen | Lung | Spleen |
| 1 | (I) in combination with RIF + PYR | | | | |
| | 12.5 | 0.52 + 1.06 | 0.35 + 0.79 | 0.88 + 1.20 | 0.90 + 1.02 |
| | 6.25 | 1.768 + 1.6 | 1.48 + 1.4 | 1.23 + 1.14 | 1.6 + 1.08 |
| | 3.12 | 2.35 + 0.35 | 2.16 + 0.37 | 2.51 + 0.39 | 2.49 + 0.38 |
| 2 | RIF + PYR | 2.67 + 0.32 | 2.47 + 0.37 | 3.34 + 0.50 | 3.2 + 0.32 |
| 3 | Control | | | | |
| | Early | 5.97 + 0.39 | 5.74 + 0.21 | 6.058 + 0.41 | 5.83 + 0.30 |
| | Late | 7.23 + 0.34 | 7.06 + 0.21 | 7.31 + 0.42 | 7.23 + 0.52 |

(I) = Compound of Formula (I);
RIF = Rifampicin;
PYR = Pyrazinamide

Pharmacokinetic Studies on the Combination

Preliminary pharmacokinetics studies of the combination of the compound of formula (I) with rifampicin and pyrazinamide was performed in mice and dog to determine bioavailibility and serum levels achieved and maintained by the combination of compounds.

The results of the study summarized in Table-XIV show that on adminstration of the combination of compound of formula (I) with rifampicin and pyrazinamide there is approximately twelve fold increase in the $C_{max}$ value of compound of formula (I) in blood. Similar improvement is also observed for the T1/2 and AUC values. The results are summarized in Table-XIV.

TABLE XIV

The Pharmacokinetic Activity Of A Combination Of Compound Of Formula (I) With Rifampicin And Pyrazinamide In Mice

| Animal | Route of Administration | Compound | Dose (mg/kg) | $C_{max}$ (µg/ml) | T½ (hr) | $T_{max}$ | AUC (hr * µg/ml) |
|---|---|---|---|---|---|---|---|
| Mice | Oral | (I) | 25.0 | 2.68 | 3.41 | 2.0 | 6.88 |
|  |  |  | 12.5 | 0.66 | 5.34 | 1.5 | 2.21 |
| Mice | Oral | (I) | 12.5 | 7.58 | 6.73 | 2.12 | 36.48 |
|  |  | RIF | 20.0 | 19.26 | 7.62 | 3.25 | 195.40 |
|  |  | PYR | 150.0 | 145.94 | 2.05 | 1.0 | 477.07 |
| Mice | Oral | RIF | 20.0 | 15.21 | 8.92 | 2.3 | 147.82 |
|  |  | PYR | 150.0 | 137.81 | 2.09 | 1.5 | 648.89 |

(I) = Compound of Formula (I);
RIF = Rifampicin;
PYR = Pyrazinamide

Acute Toxicity Studies of the Combination

A combination of the compound of formula (I) with isoniazid, rifampicin and pyrazinamide was administered as a single oral dose in Swiss albino mice. The mice were observed for 14 days. No clinical symptoms or mortality was observed. The mice were sacrificed on day 15, but no pathological changes were seen in any organ. The preliminary results obtained are summarized in Table-XV.

TABLE XV

Preliminary Acute Toxicity Studies Of The Combination Of Compound Of Formula (I) With Isoniazid, Rifampicin And Pyrazinamide

| S.No. | Compound | Animal | Route of Administration | $LD_0$ values (mg/kg) |
|---|---|---|---|---|
| 1 | (I) + INH + RIF + PYR | Mice | Oral | >2000 |
| 2 | (I) + INH + RIF + PYR | Mice | IV | >200 |

(I) = Compound of Formula (I);
INH = Isoniazid;
RIF = Rifampicin;
PYR = Pyrazinamide In addition, the combination of a compound of formula (I) with the known antitubercular first line drugs is non-genotoxic as it was found to be negative in the in vivo micronucleus test.

From the foregoing discussion, it is abundantly evident that the combinations and the pharmaceutical composition of the present invention comprising a combination of N-(3-[[4-(3-trifluoromethylphenyl)piperazinyl]methyl]-2-methyl-5-phenyl-pyrrolyl)-4-pyridylcarboxamide of formula (I) or a pharmaceutically acceptable non-toxic salt thereof with currently prescribed first line antitubercular drugs such as isoniazid, rifampicin, ethambutol and pyrazinamide, a) provides a highly effective treatment of tuberculosis including latent tuberculosis and the multi-drug resistant varieties, which is superior to that obtained with the use of currently prescribed drugs;

b) unlike the currently prescribed drugs the combinations and compositions are highly effective in the inhibition and/or treatment of mycobacterial conditions/cells including but not limited to sensitive and multi-drug resistant strains of *Mycobacterium tuberculosis, Mycobacterium avium*-intracellular complex, *M. fortutium, M. kansasaii* and other related mycobacterial species;

c) unlike the currently prescribed drugs, the combinations and compositions are highly effective in prevention of relapse of *M. tuberculosis* infection after the withdrawal of the treatment;

d) is "fast acting", thereby reducing significantly the time taken to provide complete and effective eradication of *Mycobacterium* from a subject compared to that taken by the known drugs currently in practice, either taken alone or in combination with each other. The time taken for treatment with the combination or pharmaceutical composition is only one third of that taken by the currently prescribed drugs with complete eradication of sensitive and drug resistant *M. tuberculosis;* e) a therapeutically effective amount of compound of formula (I) is found to provide a synergistic effect when it is co-administered with some of the currently prescribed first line antitubercular drugs, such as isoniazid, rifampicin, ethambutol and pyrazinamide. The synergistic effect is greater than the therapeutic effect obtained on administration of an effective amount of either compound (I), or the therapeutic effective amount of any of the first line antitubercular drugs administered individually. Further, the therapeutic effect of co-administering a compound of formula (I) and the first line antitubercular drugs, mentioned hereinabove above is greater than the therapeutic effect obtained on adminstration of the first line antitubercular drugs, when administered in combination of one another;

f) synergy being advantageous in that it allows for administration of each of the component in the combination in an amount less than that would be required if administered individually, thereby making the therapy effective for subjects who for example, do not respond adequately to the use of one component at the maximal strength dose; and/or g) allowing the administration of the individual components in lower amounts relative to the case where combined effects are additive resulting in minimization of side effects associated with the currently practiced therapy.

What is claimed is:

1. An antitubercular combination comprising a therapeutically effective amount of N-(3-[[4-(3-trifluoromethylphenyl) piperazinyl]methyl]-2-methyl- 1-5-phenyl-pyrrolyl)-4-pyridylcarboxamide of formula (I) or a pharmaceutically acceptable non-toxic salt thereof

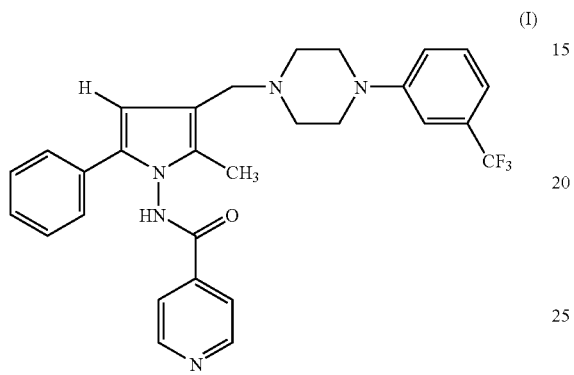

(I)

and a therapeutically effective amount of one or more first line antitubercular drugs selected from the group consisting of isoniazid, rifampicin, ethambutol and pyrazinamide.

2. An antitubercular pharmaceutical composition comprising an antimycobacterial combination of claim 1 in admixture with a pharmaceutically acceptable excipient.

3. An antitubercular pharmaceutical composition according to claim 2, wherein the pharmaceutically acceptable excipient is selected from an antioxidant, an inert diluent, a surfactant, a lubricating agent and an opacifier.

4. An antitubercular combination according to claim 1, useful for effective treatment of tuberculosis.

5. An antitubercular combination according to claim 1, for treatment of mycobacterial conditions/cells selected from sensitive and multi-drug resistant strains of *Mycobacterium tuberculosis, Mycobacterium avium*-intracellular complex, *M fortutium, M kansasaii* and other related mycobacterial species.

6. The antitubercular pharmaceutical composition according to claim 2, useful for effective treatment of tuberculosis.

7. The antitubercular composition according to claim 2, for treatment of mycobacterial conditions/cells selected from sensitive and multi-drug resistant strains of *Mycobacterium tuberculosis, Mycobacterium avium*-intracellular complex, *M fortutium, M kansasaii* and other related mycobacterial species.

8. The antitubercular combination according to claim 1, which completely eradicates sensitive and drug resistant *M tuberculosis* on completion of the treatment.

9. The antitubercular pharmaceutical composition according to claim 2, which completely eradicates sensitive and drug resistant *M. tuberculosis* on completion of the treatment.

10. A process for preparation of an antitubercular pharmaceutical composition comprising combining a compound of formula I or a pharmaceutically acceptable salt thereof

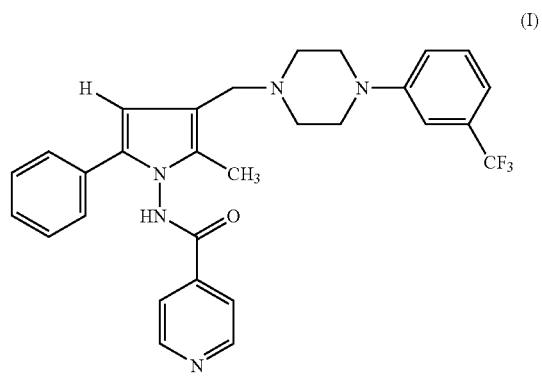

(I)

and one or more of the first line antitubercular drugs selected from the group consisting of isoniazid, rifampicin ethambutol and pyrazinamide using a dry granulation method, a wet granulation method or a direct compression method.

11. A method for treating tuberculosis comprising co-administering to a patient in need of such treatment an effective amount of: (i) a compound of formula (I) or a pharmaceutically acceptable non-toxic salt thereof

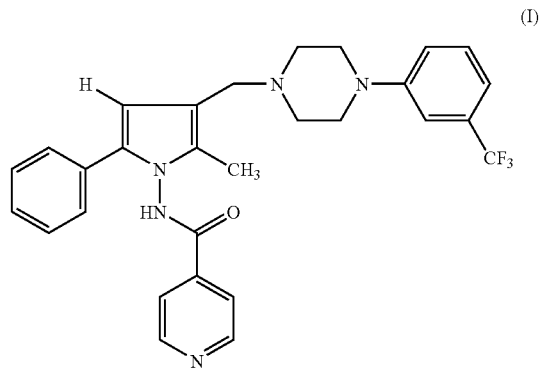

(I)

and (ii) one or more of first line antitubercular drugs selected from the group consisting of isoniazid, rifampicin, ethambutol and pyrazinamide.

12. The method as claimed in claim 11, wherein (i) and one or more of the first line antitubercular drugs are each administered orally.

13. The method as claimed in claim 11, wherein (i) and one or more of the first line antitubercular drugs are administered together in a composition.

14. The method as claimed in claim 11, wherein (i) and one or more of the first line antitubercular drugs are administered separately.

15. The method as claimed in claim 11, wherein (i) and at least one of the first line antitubercular drugs are administered together and another of the first line antitubercular drugs is administered separately.

16. The method as claimed in claim 11, wherein the tuberculosis is caused by a multi-drug resistant strain of mycobacteria.

17. The method as claimed in claim 11, wherein the tuberculosis is latent tuberculosis.

18. The method as claimed in claim 11, which completely eradicates sensitive and drug resistant *M tuberculosis* on completion of the treatment.

19. The method as claimed in claim 11, wherein the patient is treated for between two to three months.

20. A combination according to claim 1, comprising a compound of formula (I) or a pharmaceutically acceptable non-toxic salt thereof and rifampicin.

21. A combination according to claim 1, comprising a compound of formula (I) or a pharmaceutically acceptable non-toxic salt thereof and isoniazid.

22. A combination according to claim 1, comprising a compound of formula (I) or a pharmaceutically acceptable non-toxic salt thereof, isoniazid and rifampicin.

23. A combination according to claim 1, comprising a compound of formula (I) or a pharmaceutically acceptable non-toxic salt thereof, isoniazid, rifampicin and pyrazinamide.

24. A combination according to claim 1, comprising a compound of formula (I) or a pharmaceutically acceptable non-toxic salt thereof, pyrazinamide and ethambutol.

25. A combination according to claim 1, comprising a compound of formula (I) or a pharmaceutically acceptable non-toxic salt thereof, rifampicin and pyrazinamide.

26. A combination according to claim 1, comprising 12.5 or 25.0 mg/kg of compound of formula (I) or a pharmaceutically acceptable non-toxic salt thereof and 20.0 mg/kg of rifampicin.

27. A combination according to claim 1, comprising 12.5 or 25.0 mg/kg of compound of formula (I) or a pharmaceutically acceptable non-toxic salt thereof and 25.0 mg/kg of isoniazid.

28. A combination according to claim 1, comprising 12.5 or 25.0 mg/kg of compound of formula (I) or a pharmaceutically acceptable non-toxic salt thereof and 25.0 mg/kg of isoniazid and 20.0 mg/kg of rifampicin.

29. A combination according to claim 1, comprising 12.5 or 25.0 mg/kg of compound of formula (I) or a pharmaceutically acceptable non-toxic salt thereof, 25.0 mg/kg of isoniazid, 20.0 mg/kg of rifampicin and 150.0 mg/kg of pyrazinamide.

30. A combination according to claim 1, comprising 12.5 or 25.0 mg/kg of compound of formula (I)) or a pharmaceutically acceptable non-toxic salt thereof, 150.0 mg/kg of pyrazinamide and 100.0 mg/kg of ethambutol.

31. A combination according to claim 1, comprising 3.12, 6.25 or 12.5 mg/kg of compound of formula (I) or a pharmaceutically acceptable non-toxic salt thereof, 250.0 mg/kg of isoniazid, 20.0 mg/kg of rifampicin and 150.0 mg/kg of pyrazinamide.

32. A combination according to claim 1, comprising 3.12, 6.25 or 12.5 mg/kg of compound of formula (I) or a pharmaceutically acceptable non-toxic salt thereof, 20.0 mg/kg of rifampicin and 150.0 mg/kg of pyrazinamide.

* * * * *